(12) United States Patent
Liu et al.

(10) Patent No.: US 10,136,832 B2
(45) Date of Patent: Nov. 27, 2018

(54) REAL-TIME STIMULATION ARTIFACT SUPPRESSION FOR SIMULTANEOUS ELECTROPHYSIOLOGICAL ELECTRICAL STIMULATION AND RECORDING

(71) Applicant: THE REGENTS OF THE UNIVERSITY OF CALIFORNIA, Oakland, CA (US)

(72) Inventors: Wentai Liu, Los Angeles, CA (US); Yi-Kai Lo, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 25 days.

(21) Appl. No.: 15/481,715

(22) Filed: Apr. 7, 2017

(65) Prior Publication Data
US 2017/0273594 A1   Sep. 28, 2017

Related U.S. Application Data

(63) Continuation of application No. PCT/US2015/052343, filed on Sep. 25, 2015.
(Continued)

(51) Int. Cl.
*A61B 5/05*   (2006.01)
*A61B 5/053*  (2006.01)
(Continued)

(52) U.S. Cl.
CPC .......... *A61B 5/0531* (2013.01); *A61B 5/4238* (2013.01); *A61B 5/4255* (2013.01);
(Continued)

(58) Field of Classification Search
None
See application file for complete search history.

(56) References Cited

U.S. PATENT DOCUMENTS

| 2002/0077670 A1 | 6/2002 | Archer |
| 2006/0173496 A1 | 8/2006 | Lombardi |
| 2007/0118047 A1 | 5/2007 | Tracey |

FOREIGN PATENT DOCUMENTS

| EP | 2165648 A1 | 3/2010 |
| JP | 2004249080 A | 9/2004 |

(Continued)

OTHER PUBLICATIONS

Korean Intellectual Property Office (KIPO), International Search Report and Written Opinion, dated Jan. 12, 2016, counterpart PCT International Application No. PCT/US2015/052343, pp. 1-13, with claims searched, pp. 14-18.
(Continued)

*Primary Examiner* — Ankit D Tejani
(74) *Attorney, Agent, or Firm* — O'Banion & Ritchey LLP; John P. O'Banion

(57) ABSTRACT
A system and method of suppressing stimulation artifacts when performing electrophysiological electrical stimulation and recording. An artifact waveform is captured associated with a stimulus output, and then the artifact waveform calibrated during another stimulus output for accurately representing the actual artifact waveform received within each measured response to a stimulus. During actual stimulus generation and response recording, the calibrated artifact waveform is subtracted in at least one of the amplifier stages so that the artifacts are removed from the amplified response to the stimulus thus providing an accurate output without saturating the amplifiers.

14 Claims, 16 Drawing Sheets

Related U.S. Application Data

(60) Provisional application No. 62/062,309, filed on Oct. 10, 2014.

(51) Int. Cl.
*A61B 5/00* (2006.01)
*A61N 1/36* (2006.01)

(52) U.S. Cl.
CPC ............ *A61B 5/721* (2013.01); *A61B 5/7225* (2013.01); *A61B 5/7278* (2013.01); *A61N 1/36125* (2013.01); *A61B 2560/0223* (2013.01)

(56) References Cited

FOREIGN PATENT DOCUMENTS

| WO | 2014134075 A1 | 9/2014 |
| WO | 2015168162 A1 | 11/2015 |

OTHER PUBLICATIONS

European Patent Office (EPO), Communciation (The extended European search report) dated May 14, 2018, related European patent application No. 15849158.9, pp. 1-6, claims searched, pp. 7-10.

Randal cell

Induced voltage on electrode

Step current stimulus

REAL-TIME STIMULATION ARTIFACT SUPPRESSION FOR SIMULTANEOUS ELECTROPHYSIOLOGICAL ELECTRICAL STIMULATION AND RECORDING

CROSS-REFERENCE TO RELATED APPLICATIONS

This application is a 35 U.S.C. § 111(a) continuation of PCT international application number PCT/US2015/052343 filed on Sep. 25, 2015, incorporated herein by reference in its entirety, which claims priority to, and the benefit of, U.S. provisional patent application Ser. No. 62/062,309 filed on Oct. 10, 2014, incorporated herein by reference in its entirety. Priority is claimed to each of the foregoing applications.

The above-referenced PCT international application was published as PCT International Publication No. WO 2016/057244 on Apr. 14, 2016, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technological Field

This technical disclosure pertains generally to functional electrical stimulation and electrophysiological recording devices for biomedical applications, and more particularly to recording immediate electrophysiological responses during or after stimulation.

2. Background Discussion

Recording during or immediately after electrical stimulation of neural tissues allows researchers to investigate the sophisticated dynamics of neural networks for future prosthetic devices and biomedical implants. However, the recorded neural responses are often obscured by large stimulation artifacts. Stimulation artifacts arise due to either current or voltage stimulus passing through the electrode-tissue interface. The largest artifact usually appears at the site of the stimulation electrode with degraded intensity in surrounding tissues. In one example, a 100 μA current stimulus injecting into an electrode of 10k ohm impedance resulted in an artifact of approximately 1 V at the electrode and attenuated at sites away from the electrode position. Thus, removing and minimizing the artifact is important to reliably and faithfully record and analyze the neural signal.

Approaches have been attempted for using software-based methods to recover the neural signal; however, these methods tend to be time consuming. More problematic is that the artifact amplitude is typically larger (often significantly) than the neural signal of interest, so that if the neural signal amplifier provides even a moderate gain, a severe saturation of the amplifier can result because of the presence of artifacts. Once the amplifier is saturated, the neural signal is lost and cannot be recovered with software-based post-processing.

In addition, even if the amplifier is not saturated in the process, the neural signal of interest is often attenuated/distorted due to the gain desensitization of an amplifier. The gain of an amplifier is desensitized when a larger interference is presented together with the small signal of interest. For illustration, given an amplifier as a linear-time-invariant system with input of x(t) and output of v(t), v(t) this can be expressed as follows:

$$Y(t) = \partial_1(X_1(t) + X_2(t)) + \partial_2(X_1(t) + X_2(t))^2 + \partial_3(X_1(t) + X_2(t))^3 + \ldots \quad (b)$$

$$= \partial_1(A_1\cos\varpi_1 t + A_2\cos\varpi_2 t) + \partial_2(A_1\cos\varpi_1 t + A_2\cos\varpi_2 t)^2 + \ldots$$

$$\partial_3(A_1\cos\varpi_1 t + A_2\cos\varpi_2 t)^3 + \ldots$$

$$= (\partial_1 A_1 - 0.75\partial_3 A_1^3 - 1.5\partial_3 A_1 A_2^2)\cos\varpi_1 t + \ldots$$

where cos ωt represents the input signal x(t), αi is the gain at the i-th harmonic frequency of x(t), A1 and A2 are amplitudes of the neural signal and artifact, respectively. With a amplifier of a very low total harmonic distortion (THD) of 0.1% and a amplitude ratio of artifact-to-signal amplitude (A2/A1) of about 24.5, then y(t) is approximately 0, implying that the neural signal is lost as early as in the front-end amplifier stage. Moreover, in reality, the amplitude of the spikes are less than about 1 mV, while the artifact amplitude is typically ranging from tens (10s) to hundreds (100s) of mV.

Hardware approaches have also been reported to remove/reduce artifacts, such as blinking and electrode discharging. However, these approaches inevitably result in a signal loss since the amplifier cannot record a proper signal due to its saturation or input grounding during and shortly after stimulation. On the other hand, spectral cancellation of the artifact has also been implemented in the frequency domain, but this results in distortion as the spectrum of the signal of interest might overlap with that of the artifact.

Subtracting artifacts in the time domain, by creating an artifact template has also been adopted. This approach provides the potential to completely remove the artifact, yet this heavily depends on an effective means to acquire an accurate artifact template. This is further complicated by the intensity of the stimulation artifact, whose amplitude varies with distance between the recording electrode and the stimulation electrode. When attempting to use the same electrode for both neural recording and stimulation, a large artifact is inevitable, saturating the recording device. Equally important, in the process of acquiring stimulation artifact template, neural signals of interest must be exclusive.

In one attempted solution, a train of sub-threshold stimulus pulses are applied to acquire an artifact template and to avoid evoking actual neural responses. The template is then amplified based on the ratio of actual stimulus to sub-threshold stimulus for artifact cancellation. Nonetheless, a sub-threshold stimulus still effects the dynamic of neural tissue (for example, the threshold of excitability of the tissue is changed under sub-threshold stimulation). Electrode-tissue interface is also not a linear system, such that the artifact template acquired using sub-threshold stimulation cannot be generalized to present the practical artifact induced by larger stimulus intensity. In the above approach a certain period of time is further required in the training phase, preventing the scheme from adapting to different stimulus parameters swiftly.

A motion artifact is also an issue. Motion artifact is incurred due to the deformation of the soft biological tissue underneath the recording electrode or the change of contact area between the electrode and targeted tissue. This deformation or contact area change (e.g., skin stretch and relax, cortical tissue micro vibration, etc.) thus creates an undesired electrical potential change contaminating the signal of interest. For example, for a fixed amount of electrical charge accumulated on the human skin, the skin stretch would create a change of its equivalent capacitance, resulting in a voltage perturbation on the skin (i.e., motion artifact). Characterizing this impedance change in terms of its equivalent circuit model thus provides a motion artifact template that can be used to subtract the artifact from the empirical recording signals.

Accordingly, a need exists for a practical method and apparatus for real-time both stimulation and motion artifact suppression performed during simultaneous electrical stimulation and recording. The present disclosure overcomes the shortcomings of prior approaches while providing additional benefits.

BRIEF SUMMARY

A system (e.g., system, method, and/or apparatus) is disclosed for canceling physiological signal recording noise which arises in response to motion and stimulation artifacts. The system can be implemented in a variety of biomedical implantable devices. For example, the motion and stimulation artifact cancellation system can be embedded within a physiological recording and stimulation system.

The disclosed technology is an effective, low-power, hardware solution that can eliminate both motion and stimulation artifacts from physiological recordings. Compared to the state of the art, the disclosed apparatus can utilize a lower resolution ADC and DAC, performs cancellation in real-time, and prevents amplifier oversaturation. It does not rely on complex circuitry to analyze imaginary and real components of the impedance signal. Instead, estimations of skin impedance and motion artifacts are generated for use in performing the real-time noise cancellations. In one embodiment, a square current pulse is generated by the stimulator from which more accurate skin impedance and motion artifact estimates are generated, and from which a more accurate signal is created by acquiring the equivalent circuit component of the skin impedance.

Further aspects of the presented technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The disclosed technology will be more fully understood by reference to the following drawings which are for illustrative purposes only:

DETAILED DESCRIPTION

1. Artifact Suppression During Stimulation and Recording.

In this disclosure, a method and apparatus are described for artifact removal/reduction during simultaneous real-time electrophysiological electrical stimulation and recording. The disclosed approach is also beneficial when the stimulation artifact and the neural signal overlap in the time domain. The disclosure aids in handling motion artifacts which are predicted by measuring the electrode-tissue impedance variation. Unlike other approaches involving injecting a fixed-frequency sinusoidal signal to derive the impedance and requiring sophisticating computation, in this disclosure a square current stimulus is adopted to characterize the equivalent circuit.

The disclosed method and apparatus incorporates: (a) an artifact template acquisition method to avoid sub-threshold stimulation, (b) an efficient and low-cost hardware concept and implementation, (c) matching reconstructed artifact to real stimulus artifact, and (d) storage of artifact templates for various stimulus patterns.

Acquiring an appropriate artifact template without simultaneously capturing neural responses is one of the critical components for artifact removal. In contrast to using a train of sub-threshold stimulus, the present disclosure utilizes the characteristic of amplitude filtering embedded in the analog-to-digital converter (ADC). Unlike other approaches, a stimulus is utilized herein that provides sufficient intensity to evoke neural response for artifact acquisition. Since the neural signal is around the range of 1 mV, the least-significant bit of the ADC is set to be larger than the maximal neural response, serving as an amplitude filter. For example, a 10-bit ADC with 3.3 V dynamic range (LSB of approximately 3.2 mV) can be used to discard evoked neural responses. The ADC then digitizes the artifact only for further processing. Using this approach, an appropriate artifact template without neural responses can thus be derived.

Figure 1:
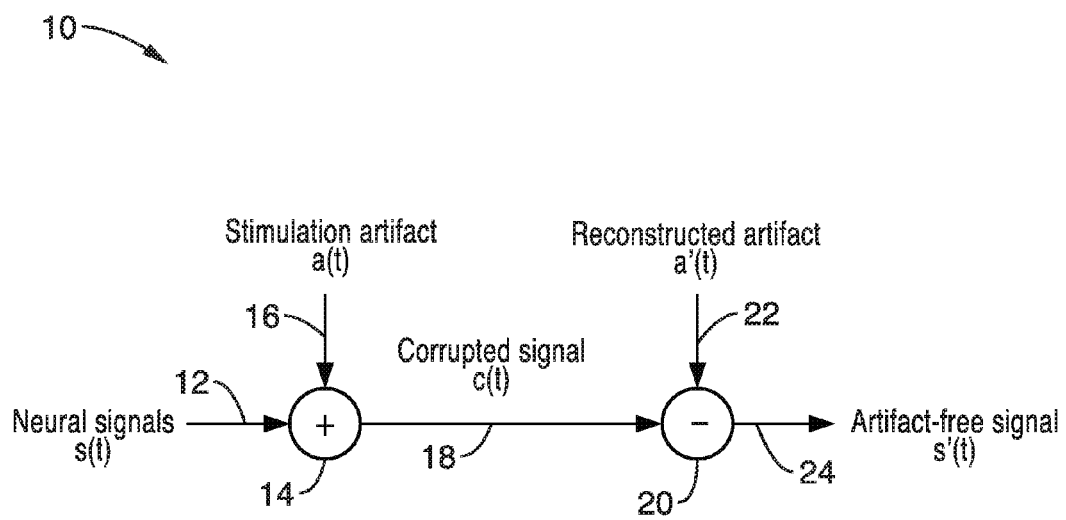
FIG. 1 is a schematic of a process of correcting stimulation artifacts with a reconstructed artifact utilized according to an embodiment of the present disclosure.

FIG. 1 illustrates an example embodiment 10 of artifact removal/reduction according to the present disclosure. A neural signal s(t) 12 is seen being summed 14 with stimulation artifact 16 producing corrupted signal c(t) 18. The corrupted signal is corrected according to the disclosure by subtracting 20 a reconstructed artifact a'(t) 22, which is generated by the system based on the empirical stimulation artifact a(t), to produce an artifact-free signal s'(t) 24. By subtracting a'(t) from the corrupted signal c(t) an artifact-free signal can be ideally recovered; however, the quality of the resultant s'(t) depends entirely on how accurately the reconstructed artifact signal a'(t) 22 resembles the stimulation artifact a(t) 16.

Figure 2:
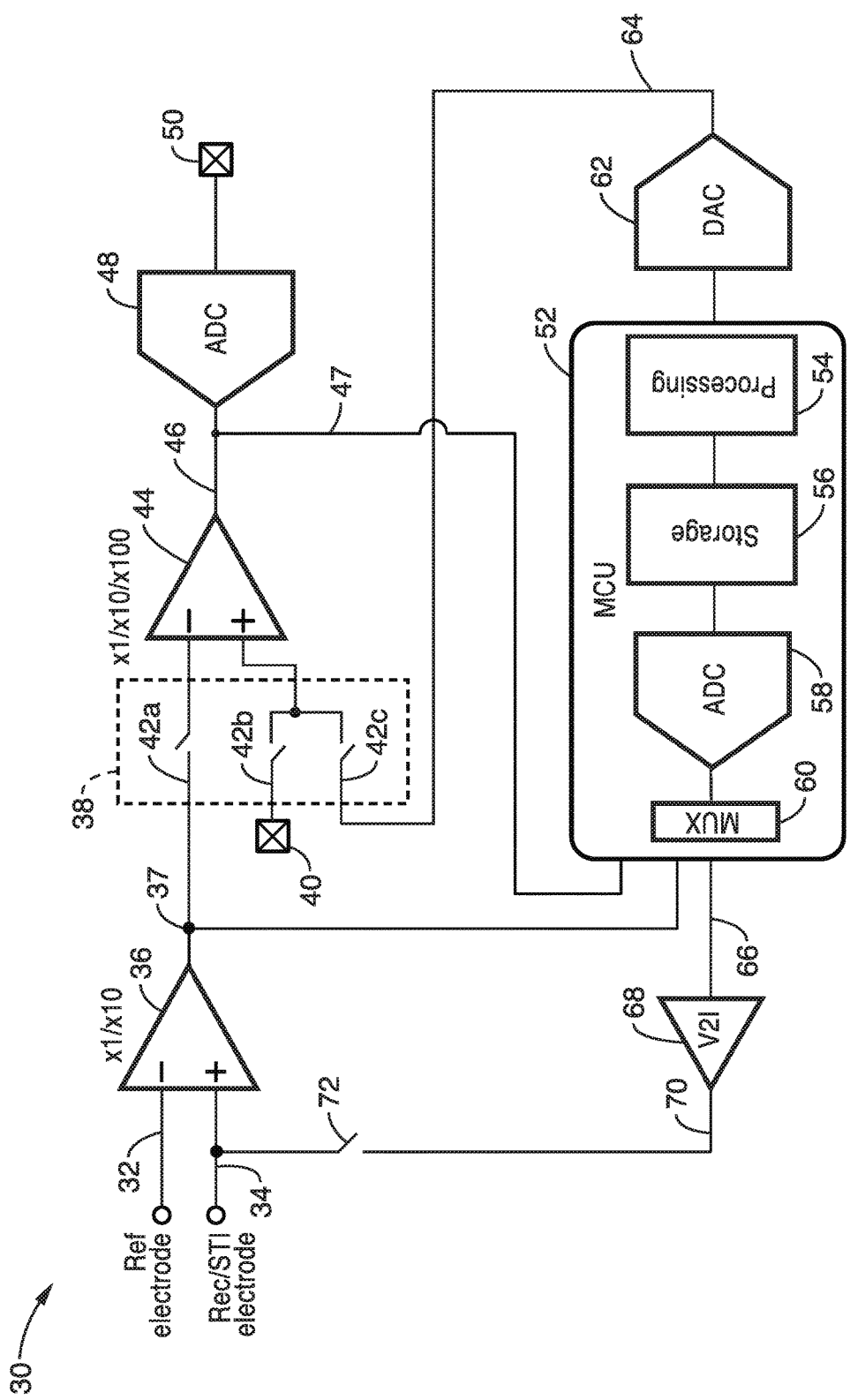
FIG. 2 is a block diagram of a circuit for correcting stimulation artifacts according to an embodiment of the present disclosure.

FIG. 2 illustrates an embodiment 30 for the disclosed artifact removal/reduction system. In general the system comprises at least two input amplifiers and a stimulus output amplifier which are controlled by control circuitry. More particularly an implementation of the system is seen in the figure comprising two amplification stages 36, 44, an analog-to-digital converter (ADC) 48, a digital-to-analog converter (DAC) 62, a stimulator 68 with output 34, and a microcontroller unit (MCU) 52 (or other means of electronic control, such as any type of CPU or DSP, FPGAs, gate arrays, logic arrays, or similar circuits utilized separately or in combination) for controlling stimulus outputs, measurement collection and artifact suppression.

Under normal operation, two inputs of the first amplifier 36 are connected to the working electrode 34 and the reference electrode 32 to pick up and amplify the neural signal. It should be appreciated that multiple amplifiers may be alternatively utilized within either the first stage or second stage of response amplification. Output from the first stage of amplification 36 is output 37, through switch 42a in a switching selector 38, to a second stage of response amplification, shown depicted as the negative terminal of a differential amplifier 44 which provides additional amplification while subtracting a selected subtraction signal input (e.g., reference, first artifact template, or second artifact template). In particular, the positive terminal of the second stage amplifier is connected to a reference voltage 40 through switch 42b, or to DAC output 64 through switch 42c. A stimulator amplifier 68 is driven from an output of MCU 52 (or similar control means) to generate a stimulator signal 70 for selective connection through switch 72 to recording/STI electrode 34.

The amplified signal 46 from the second amplifier 44 then is digitized by an analog-to-digital converter (ADC) 48 whose digital output 50 can be sent to a signal processing unit, personal computer, or other means of processing and/or storing the digitized information. Amplified signal 46 is also seen coupled 47 to an input of MUX 60 for second phase calibration purposes.

The microcontroller unit (MCU) 52 is shown having a processor 54, memory storage (data and instruction) 56, an analog-to-digital converter (ADC) 58, and a multiplexer (MUX) 60. In the process of artifact acquisition, switch 42b is on; switch 72 is also on to take stimulator output while the MCU 52 sends a control signal (i.e., stimulation parameters) to the stimulator 68. The selected input of MUX 60 is connected to amplifier 37 to read the artifact signal. ADC 58 then digitizes the artifact and stores it in the memory 56.

It will be appreciated that any desired combination of processing, storage, ADC and MUX elements can be utilized, regardless of whether incorporated in a single MCU device or a combination of multiple circuit elements. The disclosed apparatus can be readily implemented within various electrode stimulation apparatus and systems. At least one embodiment of the system is preferably implemented to include one or more computer processor devices (e.g., CPU, microprocessor, microcontroller, DSP, computer enabled ASIC, FPGA, gate arrays, logic arrays, etc.) and associated memory storing instructions (e.g., RAM, DRAM, NVRAM, FLASH, computer readable media, etc.) whereby programming (instructions) stored in the memory are executed on the processor to perform the steps of the various process methods described herein. The presented technology is non-limiting with regard to memory and computer-readable media, insofar as these are non-transitory, and thus not constituting a transitory electronic signal.

A simple electrode model (see FIG. 9A) with doubled capacitance of 100 nF, spread resistance of 10k ohm, and a faradic resistance of 1 Mohm was used in the proof-of-concept testing. The reference electrode is assumed to be relatively large allowing its impedance to be neglected. The same electrode is used for both stimulation and recording in this example to test the worst case scenario in which the largest artifact is presented in the stimulation site.

Figure 3A:
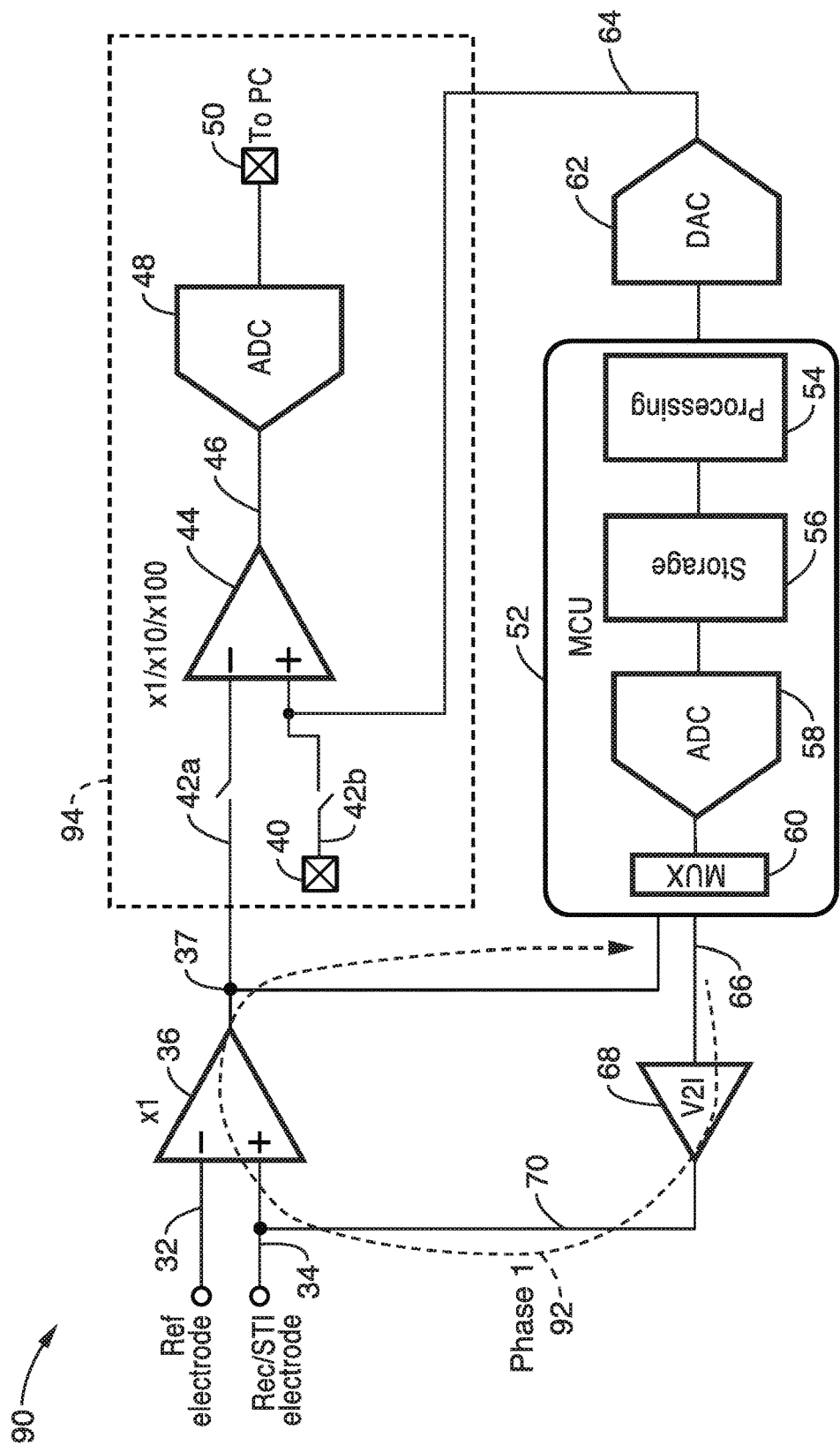
FIG. 3A and FIG. 3B are block diagrams of the circuit of FIG. 2, shown utilized in a Phase 1 and Phase 2 mode respectively, according to embodiments of the present disclosure.
Figure 3B:
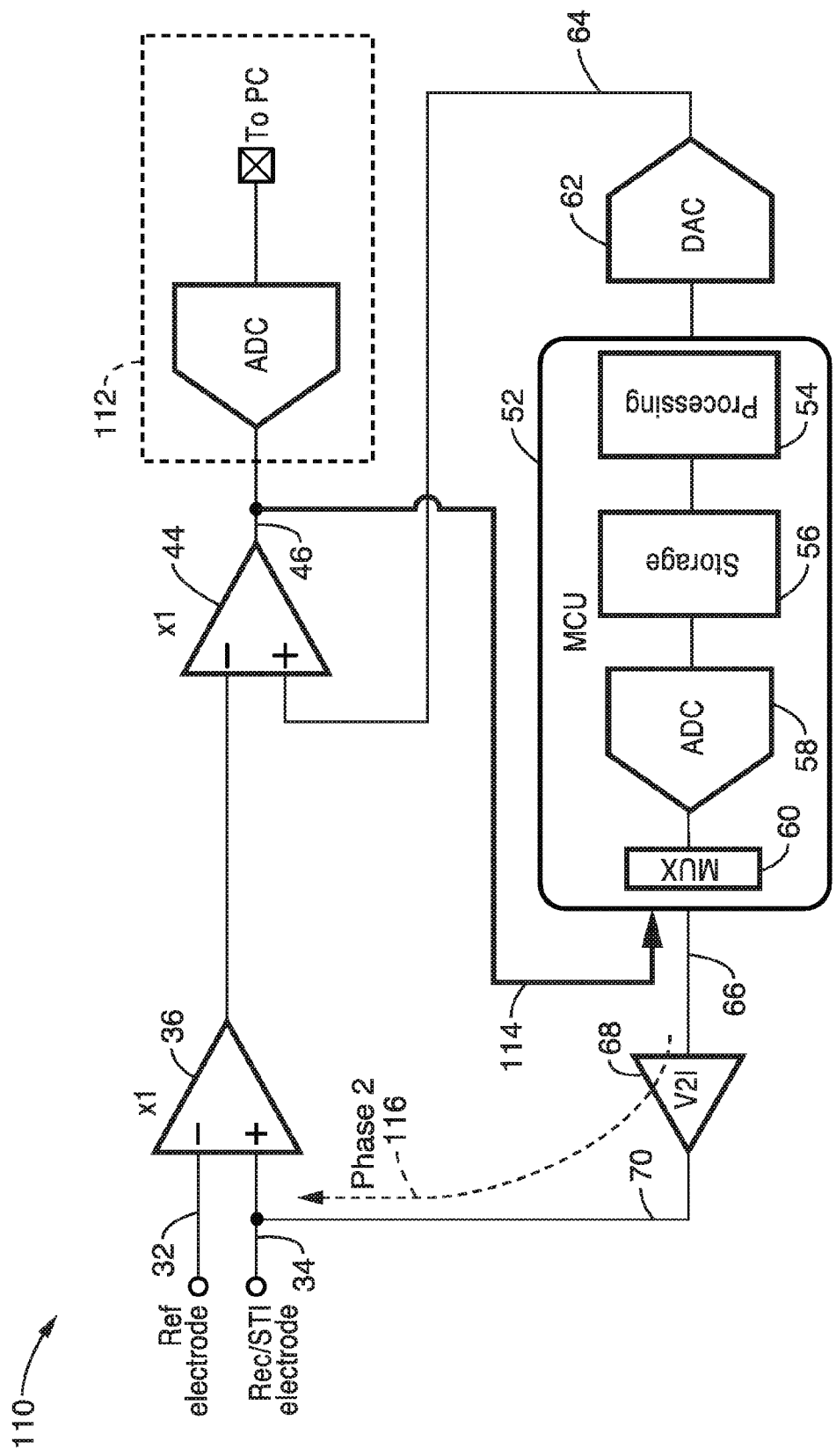
Figure 5:
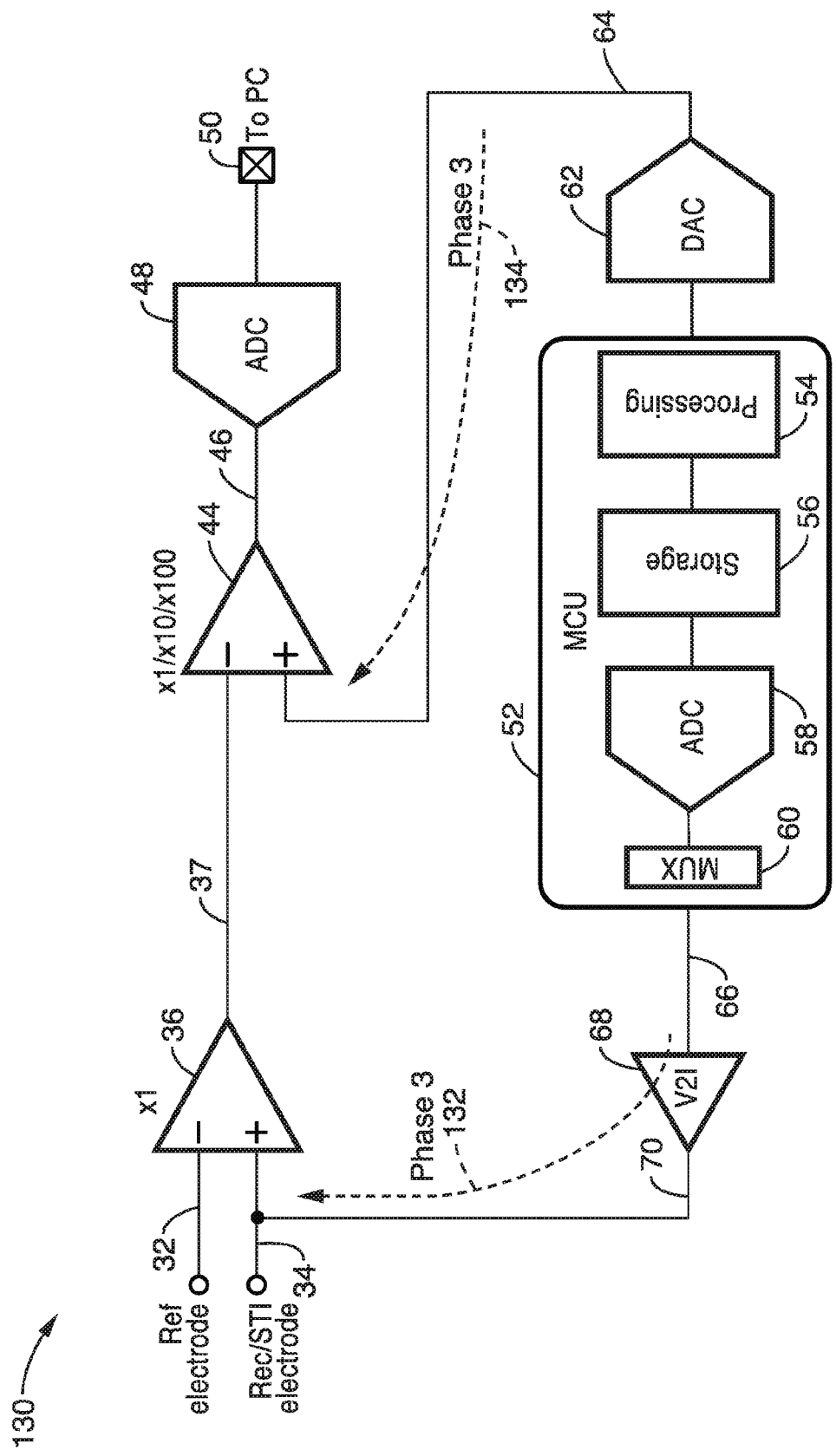
FIG. 5 is a block diagram of the circuit of FIG. 2 shown utilized in a Phase 3 mode, according to another embodiment of the present disclosure.

When the system is employed to remove/reduce an artifact, its operation can be divided into three phases, referred to herein as Phase 1, Phase 2, and Phase 3, as seen in FIG. 3A, FIG. 3B and FIG. 5, respectively.

FIG. 3A and FIG. 3B illustrate embodiments showing Phase 1 and Phase 2 paths. In FIG. 3A an embodiment 90 is seen showing a Phase 1 path 92 with the processor controlling the stimulator to generate a stimulus into the tissue to acquire the first artifact template. The recording electrode 34 is connected to the stimulator signal 70 from amplifier 68 through switch 72, while the output of the first amplifier 36 is configured as a unity gain buffer directed to a programmable second stage amplification 94. It will be readily recognized that the elements depicted in this Phase 2 path diagram represent different connections of those elements shown in FIG. 2.

FIG. 3B illustrates an embodiment 110 showing a Phase 2 path 116 in which calibration of the artifact template is performed. The second amplifier 44 is activated and configured as a unity-gain buffer and a second stimulus 70 is sent to the electrode model 34 during artifact acquisition. It should be noted that output 66 comprises one or more control signals to the voltage-to-current (V2I) (stimulator), with output 64 being the actual DAC output, sent to the input of amplifier 44. The stored artifact is converted to an analog waveform via DAC 62 and passed 64 to the positive terminal of the second amplifier 44. Thus, the artifact signal and the reconstructed artifact are subsequently subtracted inside amplifier 44 with its output 46 digitized by ADC 112 circuit and stored in the MCU. It should be appreciated that multiple calibration passes may be performed as desired, such as until a desire accuracy is verified. In addition, the artifact templates can be adjusted in any desired manner to achieve increased accuracy, such as corrections applied, use of averaging, or other statistical approaches based on multiple calibration passes. It will be recognized that the elements depicted in this Phase 2 path diagram represent different connections of those elements shown in FIG. 2. After an accurate artifact is derived, the gain of amplifier 44 can be modified based on the signals of interest to record artifact-free neural signals. This approach also allows any commercial neural recording systems to utilize the proposed artifact cancellation scheme by receiving analog output 46.

Figure 4:
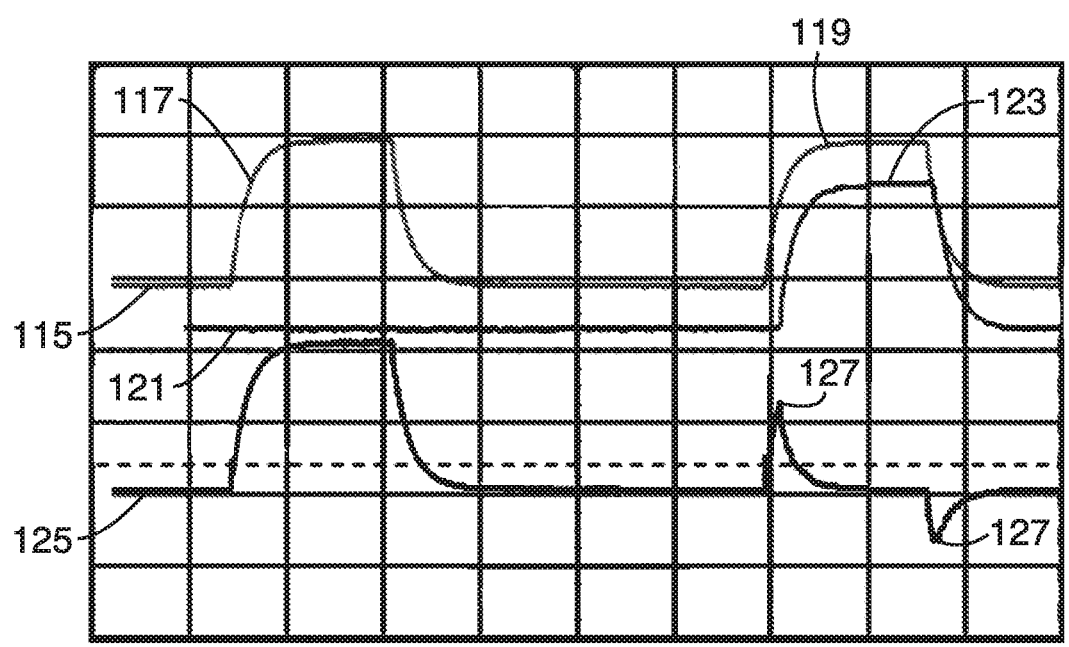
FIG. 4 is a plot of voltage waveforms for Phase 1 and Phase 2 operation of the circuit in FIG. 2.

FIG. 4 depicts waveforms associated with Phases 1 and 2. A voltage on the RC model of the electrode is seen in waveform 115 having a first artifact 117 for obtaining a' in Phase 1, and a second artifact for generating a-a' 119 in Phase 2. A reconstructed artifact waveform is shown 121 with reconstructed artifact using a' 123. In waveform 125 signal a-a' is seen at the second amplifier output which is the differential amplifier output. Artifact and neural responses are then digitized by the MCU. Note that the small neural signal can be filtered out by setting the LSB of ADC to be larger than the amplitude of neural signals. The digitized artifact template is stored in the ROM of the MCU for use in Phase 3. It should be noted that amplifier 44 output in Phase 2 use reflects the difference between the real artifact and the reconstructed artifact. A large residual artifact would overwhelm the small neural signal. It can be seen from FIG. 4 that a large residual artifact 127 remains if the artifact template acquired in Phase 1 is directly applied. To overcome this challenge, the apparatus utilizes this difference information to calibrate the first artifact template by performing a subtraction inside MCU. In the next step, the MCU updates the initial artifact template with the calibrated template.

FIG. 5 illustrates an embodiment 130 showing Phase 3 paths 132, 134 for simultaneous recording and stimulation. The stimulation path 132 amplifies stimulator signal 66 from MCU 52 through amplifier 68 to generate a stimulator pulse 70 to recording/STI electrode 34. At the same time the MCU has output the calibrated artifact 64, shown in Phase 3 path 134, to cancel the real artifact.

Figure 6A:
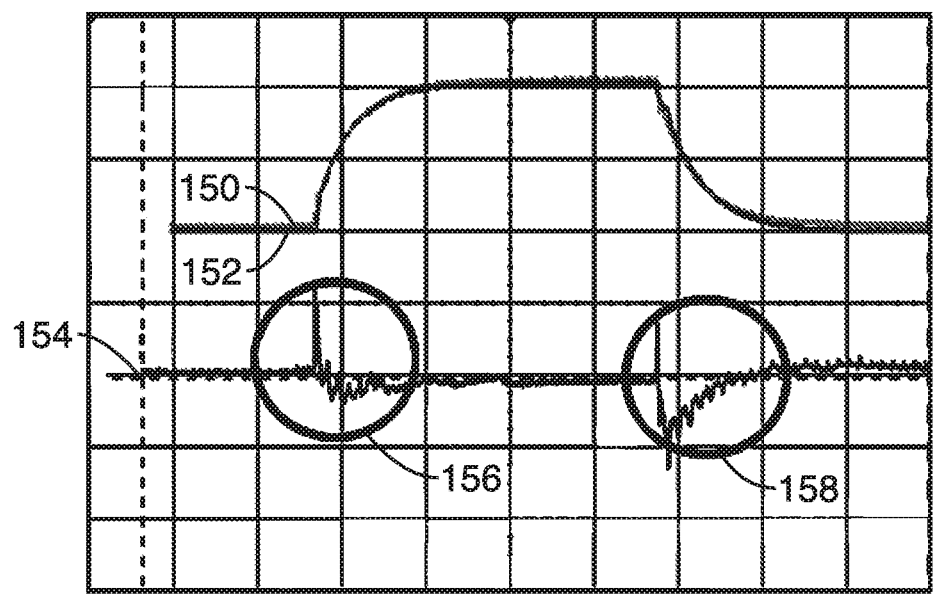
FIG. 6A and FIG. 6B are plots of voltage waveforms for Phase 3 operation depicting applying a calibrated template (FIG. 6A), and measured results with a 1 kHz input (FIG. 6B).

FIG. 6A depicts waveforms relating to Phase 3 paths. The voltage on the RC model is shown in waveform 150, which is closely paralleled by the waveform of calibrated artifact template 152. Waveform 154 depicts the second amplifier output and highlights 156, 158 the reduced difference between artifact and calibrated templates, when compared with the differences 127 seen in FIG. 4.

Figure 6B:
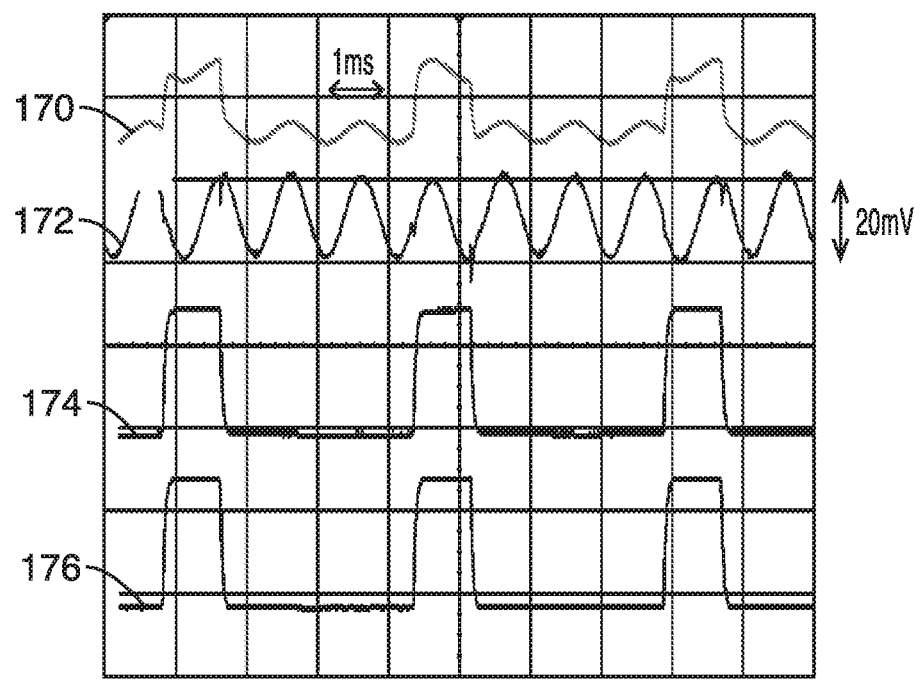

FIG. 6B depicts that by applying the calibrated artifact to the second amplifier, the residual artifact is dramatically reduced. Waveform 170 depicts signal A showing an artifact embedded in a 1 kHz sine wave output, while waveform 172 illustrates the reconstructed waveform after removal of the artifact (A-A'). With a reduced artifact amplitude, amplifier saturation can be prevented to preserve the neural signal during and after a electrical stimulus is applied. Waveform 174 depicts the artifact present on the RC model, while waveform 176 depicts a reconstructed artifact using the DAC; wherein it is noted how closely the reconstructed artifact estimates the actual artifact. These experimental results indicate how a 1 kHz sine wave is used to present the signal of interests and a current stimulus of approximately 15 μA is applied on the electrode model. It is thus clearly demonstrated that in using this technique the main features of the sine wave are well preserved.

Figure 7:
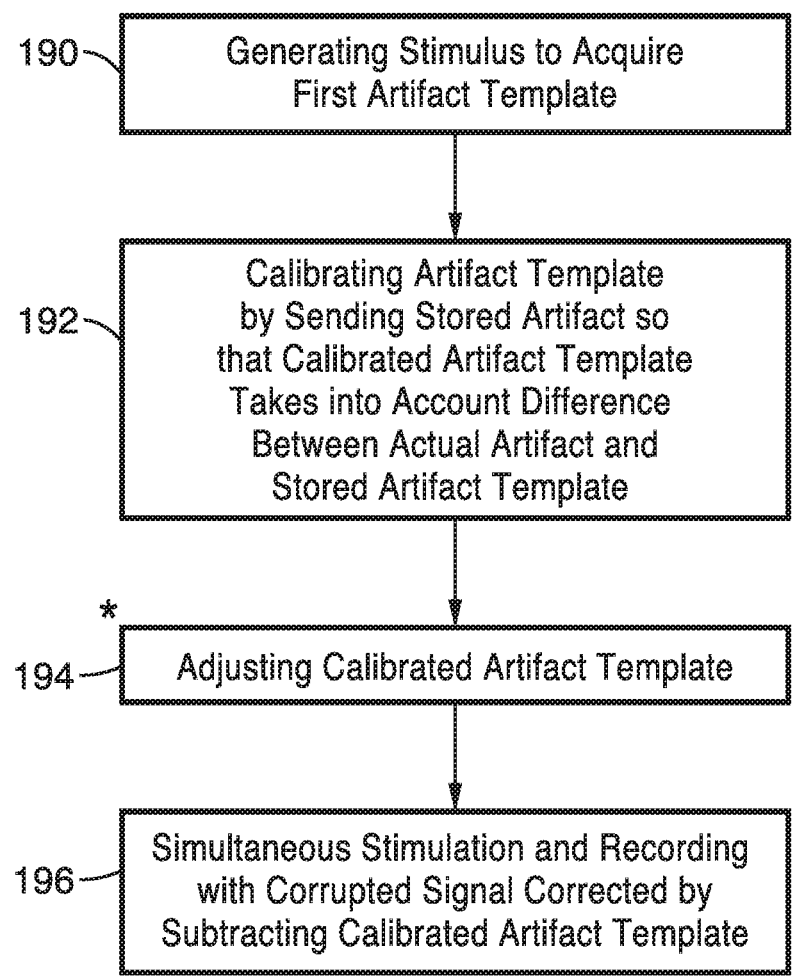
FIG. 7 is a flow diagram of steps performed during correcting stimulation artifacts with a reconstructed artifact according to an embodiment of the present disclosure.

FIG. 7 illustrates an example embodiment of generalized steps for performing artifact suppression during electrophysiological electrical stimulation and recording. A stimulus is generated 190 to acquire a first artifact template. Then this first artifact template is utilized as a signal to a differential circuit (e.g., amplifier in the embodiment shown) for obtaining a calibrated artifact template 192 which takes into account the difference between the actual artifact and the stored artifact template. Optionally, one or more mechanisms can be utilized 194, such as repeating the calibration process, averaging across multiple calibrations, or similar, to adjust the calibrated artifact template to improve its accuracy. During simultaneous stimulation and recording the corrupted signal being received is corrected 196 by subtracting out the calibrated artifact template.

It will be appreciated that in FES applications, parameters of the stimulus may be continuously changing depending on different experimental circumstances. However, if each stimulus pattern requires a certain period of training to form an artifact template, in some cases it can be difficult to modify the artifact template in real-time. However, according to the present disclosure only two stimulus are required prior to simultaneous stimulus and recording, therefore allowing a fast modification and update of the artifact template. Moreover, a look-up table can be built by finding the artifact template beforehand and storing this in MCU or other digital signal processing unit. Thus, when a known stimulus is being generated (firing), a corresponding artifact template can be readily selected for simultaneous stimulation and recording.

It will be noted that a high voltage amplifier is used to record both the neural and artifact signal, so that the amplifier provides a large input dynamic range toward avoiding saturation caused by artifacts. During artifact signal acquisition, the neural signal can be filtered/blocked by setting the least-significant bit (LSB) of the ADC to be larger than the amplitude of the neural signal. In order to acquire a more realistic artifact signal, multiple iterations of artifact template acquisition/calibration can be performed. In order to accommodate real-time electrode-tissue impedance changes, the artifact template is preferably updated periodically.

In conclusion, a novel stimulation artifact cancellation/reduction technique has been described for simultaneous recording and stimulation. With this method and apparatus, it is possible to perform recording and electrical stimulation even using the same electrode while the evoked neural signal can still be preserved. An artifact template can be derived without intervening the dynamics of neural networks and inclusion of evoked neural responses. The simple building blocks necessitated for the present disclosure can be suitably implemented in a small form factor and the use of low-cost hardware.

It should also be noted that the technology described herein does not rely on complex circuitry to analyze imaginary and real components of the impedance signal. Instead, in at least one embodiment, a simple square current pulse can be utilized from the stimulator, allowing more accurate estimations of skin impedance and motion artifacts, thereby creating a more accurate signal by acquiring the equivalent circuit component of component of the skin impedance.

The following describes methods and apparatus for impedance characterization to estimate skin impedance as may be utilized with the above artifact removal method/apparatus. However, it should be appreciated that the preceding sections describe a real-time simultaneous stimulus and measurement, with a square current pulse stimulus thus allowing extrapolation of skin/tissue impedance at different frequency(ies) using the same pulse parameters by knowing its equivalent model.

2. Bio-Impedance Measurement 2.1 Background

The following section provides supplemental information in supporting the embodiments described in Section 1 of the present disclosure, and was found in the Appendix of the provisional application to which this regular application claims priority.

The proper application of functional electrical stimulators relies on having some knowledge of the bio-impedance at the electrode-electrolyte/tissue interface. Impedance can also be utilized as a merit to: (1) evaluate the proximity between electrodes and targeted tissues, (2) estimate the safe boundary of the stimulation parameters, and/or (3) be used as a biomarker to monitor the activity of internal organs (i.e., contraction/relaxation of smooth muscles in intestine/colon/stomach) or tension of blood vessels.

One simple approach for estimating bio-impedance is based on the injection of a small sinusoidal current at a fixed frequency and the measurement of the evoked voltage at the electrode. However, this approach can only provide the information of the impedance at a given frequency without having an equivalent circuit model available.

In another approach, electrochemical impedance spectroscopy (EIS) has been widely used to derive electrode-electrolyte impedance. EIS is based on the pseudo-linearity characteristic of the electrode and a small AC potential (typically between 1 and 10 mV) is applied to excite the electrochemical cell. Nonetheless, the electrode-electrolyte/tissue impedance is not linear. Thus, doubling of excitation voltage might not necessarily double the applied current as expected, while stimulation usually evokes a large transient voltage at the electrode. Thus, EIS does not appear to be the best approach for impedance measurement of stimulation electrodes. In addition, the hardware cost of the EIS approach is high, with additional complexity being required when integrating EIS into a neural stimulator.

Bio-impedance measurement based on voltage/current pulse excitation has been proposed to infer the parameters of a three-element Randles cell electrode model. One of these proposals involves injecting a current stimulus into the electrode and measuring the resulting voltage, but only the electrode-tissue resistance can be derived. A sophisticated computation is presented in one approach, the complexity of which impeded it from being incorporating into implantable stimulators. One of these methods is capable of acquiring all parameters of a Randles cell, but a prerequisite is to deliver a stimulus with infinite pulse width to the electrode; which is both problematic to achieve and would cause an electrode overpotential higher than its water window. Therefore it is seen that numerous attempts have been made with little success in regards to determining bio-impedance.

2.2 Bio-Impedance Measurement Technique

Obtaining information about equivalent circuit parameters of an electrode is useful in a number of regards, such as electrode placement and stimulus signal generation. By utilizing equivalent circuit parameters, a safe boundary can be set for stimulus parameters in order not to exceed the water window of electrodes. An impedance measuring technique is presented with an implemented proof-of-concept system using an implantable neural stimulator and an off-the-shelf processing element (e.g., microcontroller). The technology presented yields the parameters of an electrode equivalent circuit by injecting a single low-intensity bi-phasic current stimulus, in the range of several microamps ($\mu$A) to tens of microamps, with deliberately inserted interpulse delay and by acquiring the transient electrode voltage at three well-specified timing intervals.

Use of a low-intensity stimulus allows the derivation of electrode double layer capacitance since capacitive charge-injection dominates when electrode overpotential is small. Insertion of the interpulse delay creates a controlled discharge time to estimate the Faradic resistance. The method presented has been validated by measuring the impedance of: (a) an emulated Randles cell made of discrete circuit components, and (b) utilizing a custom-made platinum electrode array to compare estimated parameters with the results derived from an impedance analyzer.

The method presented herein can be integrated into implantable or commercial neural stimulator systems with a low overhead in regards to power consumption, hardware cost, and computation. Current commercial neural stimulators can only measure electrode impedance at a given frequency. By contrast, the present disclosure yields circuit parameters which aid in determining proximity between electrodes and tissue, but also for setting stimulus parameters to prevent electrode damage.

In the present disclosure, excitation is based on using a bi-phasic current pulse with interpulse delay. The technique utilizes the electrode characteristic themselves, in which pure capacitive charge-injection dominates the initial electric charge transfer from the electrode to the tissue when the electrode overpotential is small and the faradic charge transfer process does not happen. A deliberately specified period of interpulse delay is then applied to acquire parameters of a Randles cell model of an electrode with simple computation and low hardware cost. The range of the inserted interpulse delay is mainly dependent on the size of the electrode that determines its discharge time constant, and the resolution of the off-the-shelf processing unit (i.e., microprocessor). The length of the interpulse delay must be set to ensure the decayed electrode overpotential is larger than the minimal resolution of the quantizer (i.e., analog-to-digital converter). As a rule of thumb, the maximal interpulse delay can be set as approximately 2.8 times the electrode discharge time constant.

In one embodiment, the presented technology adopts a bi-phasic current stimulus excitation to yield the parameters of the equivalent circuit model of an electrode without complex computation and hardware setup. In addition, the presented technology can be conveniently integrated into commercial systems with little extra hardware overhead, since modern stimulators are typically designed to allow for the use of generating bi-phasic current stimulus in driving an electrode. The presented technology is applicable to a wide range of stimulators, and is also applicable to implantable stimulators for prosthetic devices.

In one embodiment, to monitor the propagating activity of internal organs along the gastrointestinal track (i.e., stomach, intestine, colon) or tension of the vascular smooth muscles, simultaneous multi-site stimulation on multiple electrodes placed on top of the tissue can be performed to measure the bio-impedance change in real-time. It is important to note that stimulus delivered to these electrodes must be time-interleaved to ensure the delivered current does flow to the ground/reference electrode, instead of flowing into adjunct stimulation electrodes. The above setup enables the measurement of propagating slow waves of the gastrointestinal track or blood pressure for a closed-loop implantable stimulator. It can also be used in clinical studies on the enteric/autonomic nervous system.

Significant benefit is derived from electrode-stimulus applications when the impedance of the electrode-electrolyte interface is understood. If the circuit parameters are known, the limit of stimulus intensity and pulse width can be determined in order not to exceed the water window of the electrode underuse and the compliance voltage of the stimulator. Characterizing the electrode-electrolyte interface by the present disclosure provides benefits for additional applications as well.

It will be appreciated that the disclosed bio-impedance characterization method can be applied to various forms of implanted electrodes, for example those implanted at various locations within internal organs, such as along the digestive tract, for instance to provide tracking of smooth muscle activity along the intestines. By applying these techniques to the normal or pathological smooth muscle of internal organs (e.g., stomach, large intestine, and small intestine), the contraction/relaxation of the muscle activities can be monitored through impedance change in the electrode-electrolyte interface.

Figure 8:
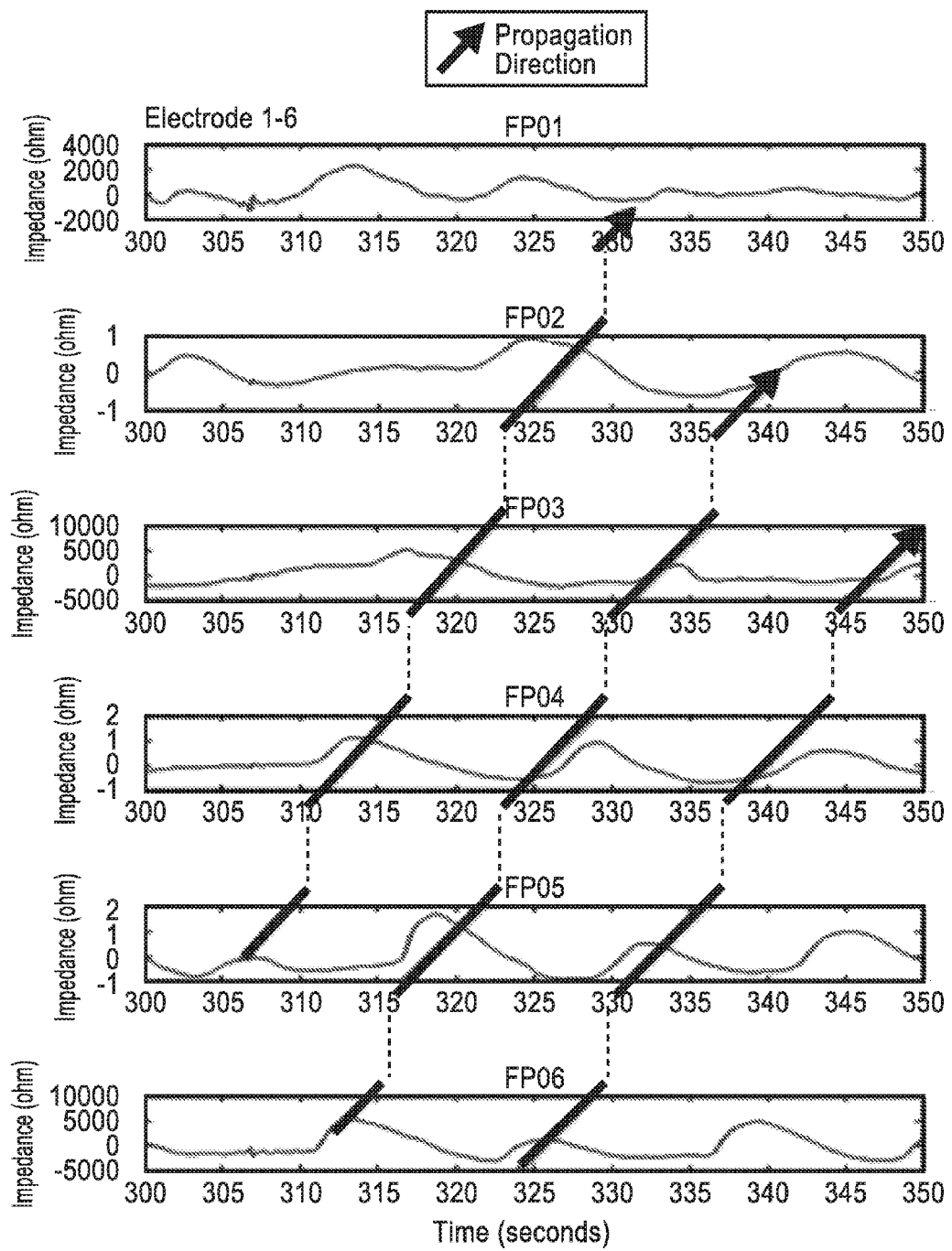
FIG. 8 are plots of impedance for a plurality of implanted electrodes along digestive internal organs as utilized within an embodiment of the present disclosure.

FIG. 8 depicts impedance changes representing the propagation of the slow-wave activity resulting from the smooth muscle contraction/relaxation for each of six implanted electrodes, with the propagation direction between channels shown by the arrows. By applying multiple-electrodes on the normal or pathological smooth muscle of internal organ (such as small and large intestine and stomach) and performing the disclosed bio-impedance measurements, the propagation of smooth muscle contraction/relaxation wave can be monitored in vivo and in vitro. This measurement ability is of significant advantage as it is currently not feasible to monitor or record intestinal activity in vivo without damaging its smooth muscles or neural networks.

In at least one embodiment, the measured impedance signal can be utilized as a feedback signal to one or more implantable devices for controlling drug delivery, or any desired means of stimuli (i.e., electrical, optical, magnetic, stimulation, and so on). In another embodiment, the same methodology can also be adopted to measure the pressure of the blood vessel, which can also be reflected from the bio-impedance variation of activating vascular smooth muscles. This serves as an alternative tool for recording smooth muscle activities, and can be performed non-invasively, in contrast to conventional methods that require inserting a pressure catheter into the target organ in order to measure a single point of pressure and thus multi-site activity monitoring with those systems is infeasible and unrealistic. The presented bio-impedance technology adopts small current, short stimulation pulses to ensure that the stimulation does not activate smooth muscle activity, while acquiring information on bio-impedance changes relating to smooth muscle activities. Moreover, the proposed method also enables the simultaneous electrical recording and stimulation through the same electrode. As stimulus with large pulse width and high intensity is usually used to activate neuron/muscles, the low-intensity and short stimulus used for bio-impedance measurement can be co-registered to the same electrode simultaneously while the artifact caused by strong stimulus can be filtered in frequency domain with ease.

Bio-impedance measurements according to the presented technology provides a number of important features. (a) Simple bi-phasic current excitation is utilized to measure bio-impedance, whereby the method is applicable for use in commercial neural stimulators. (b) Measurement based on bi-phasic current stimulus ensures the charge balance at the electrode, overcoming the problems with accumulated charge causing a DC offset at the electrode impacting the measurement of Faradic resistance when utilizing monophasic stimulation. (c) By leveraging the initial pure capacitive charging of the stimulating electrode, double layer capacitance can be readily estimated. (d) An interpulse pulse delay specified in the stimulus parameters enables the estimation of Faradic resistance. (e) The presented technique provides a way for users to set the stimulation parameters based on the electrode parameters estimated to avoid electrode or tissue damage. The following sections describe the details of this bio-impedance measurement method.

Electrical charge is delivered from an electrode through two main mechanisms: capacitive charge-injection and faradic charge injection. Bio-impedance can be schematically represented by an equivalent electrical circuit.

Figure 9A:
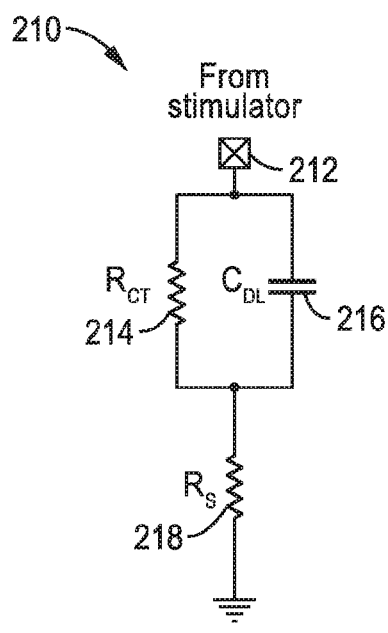
FIG. 9A through FIG. 9C are schematic and waveforms diagrams associated with a Randles cell, step current stimulus, and electrode voltage waveforms.

FIG. 9A illustrates an example embodiment 210 of a simple three-element Randles cell electrode-electrolyte model showing connection from stimulator 212 to a circuit consisting of a charge transfer resistance $R_{CT}$ 214, a double layer capacitance $C_{dl}$ 216, and a tissue-solution resistance $R_S$ 218 shown connected to ground, is herein adopted since both mechanisms are incorporated.

Figure 9B:
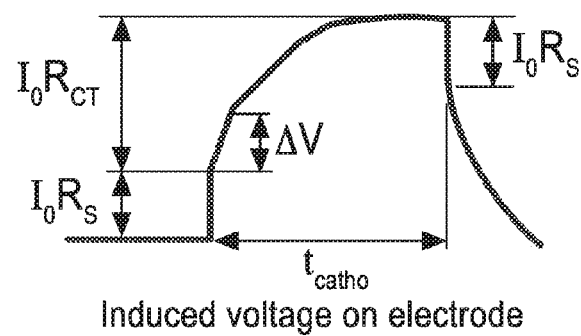
Figure 9C:
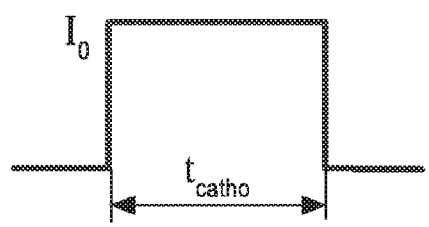

FIG. 9B and FIG. 9C depict electrode transient voltage waveform (FIG. 9B) when a single (not bi-phasic) step current stimulus is injected with intensity of $I_0$, and pulse width of $t_{catho}$. By using a Laplace transform, impedance of the electrode model and the cathodic stimulus is expressed as $R_{CT}/(1+sR_{CT}C_{dl})$ and $I_0/s$, respectively. The resulting voltage can be derived by taking inverse Laplace transform of the product of the impedance-stimulus:

$$V_e = \left(I_0 \times R_S + I_0 \times R_{CT}\left(1 - \frac{-t}{R_{CT} \times C_{dl}}\right)\right)u(t). \quad (1)$$

$I_0 R_S$ in Eq. (1) is the transient voltage increase when the instantaneous current is flowing through $R_S$. This voltage can be measured immediately after the stimulus is fired for the estimation of $R_S$. The second term in Eq. (1) results from the stimulus current which charges $C_{dl}$. As pulse-width increases, this voltage drop approaches $I_0 R_{CT}$ and reaches a plateau. After the stimulus is finished, charge stored in $C_{dl}$ is discharged through the resistive paths and the resulting voltage on the electrode gradually diminishes. It can be inferred from Eq. (1) that a stimulus with sufficiently long pulse-width can drive the subsequent voltage increase of the electrode overpotential to approach $I_0 R_{CT}$ and to allow a quick derivation of $R_{CT}$. However, this might also drive the electrode overpotential over the range of its water window, causing electrode or tissue damage. The term "water window" as utilized in regard to electrodes is the electrochemical window (EW) of a substance (e.g., water) as the voltage range between which the substance is neither oxidized nor reduced. This range is important for the efficiency of an electrode, because out of this range, water is electrolyzed. Returning back to the discussion of $R_{CT}$ it should be noted that once electrode stimulus is out of range, then $R_{CT}$ cannot be determined because $C_{dl}$ cannot be estimated based on Eq. (1).

According to the above observation, a more deliberate stimulus waveform is sought for exciting the electrode in order to yield all the parameters of the Randles cell electrode model with less computation and the prevention of electrode/tissue damage (exceeding the water-window). Herein, a bi-phasic current stimulus with interpulse delay for impedance measurement is disclosed with details provided in the following section.

By carefully investigating the transient electrode voltage shown in FIG. 9B and FIG. 9C, it can be found that after the initial electrode voltage increment of $I_0 R_S$, there is a short period of time in which the electrode voltage is linearly increasing ($\Delta V$ in FIG. 9B). This linear voltage increase is due to the pure capacitive current charging $C_{dl}$ and its value depends on the rate of potential change. Based on charge reservation, the voltage increment during this period can be expressed as:

$$\Delta V = \frac{I_0 \times t}{C_{dl}}. \tag{2}$$

Once electrode overpotential further increases, Faradic current through $R_{CT}$ starts to conduct a relatively large portion of the injected current from the stimulator and the increment of the electrode overpotential becomes non-linear.

Figure 10A:
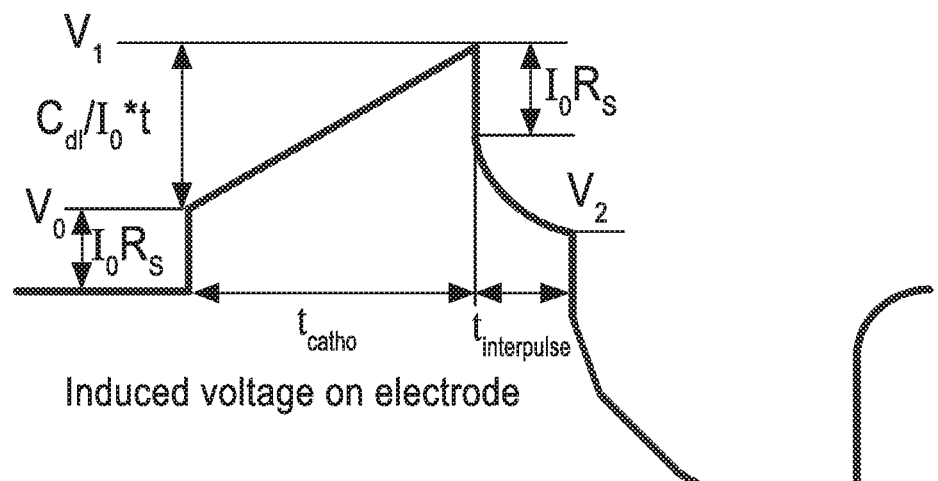
FIG. 10A and FIG. 10B are waveform diagrams of induced voltage at the electrode in response to a bi-phasic current stimulus within interpulse delay.
Figure 10B:
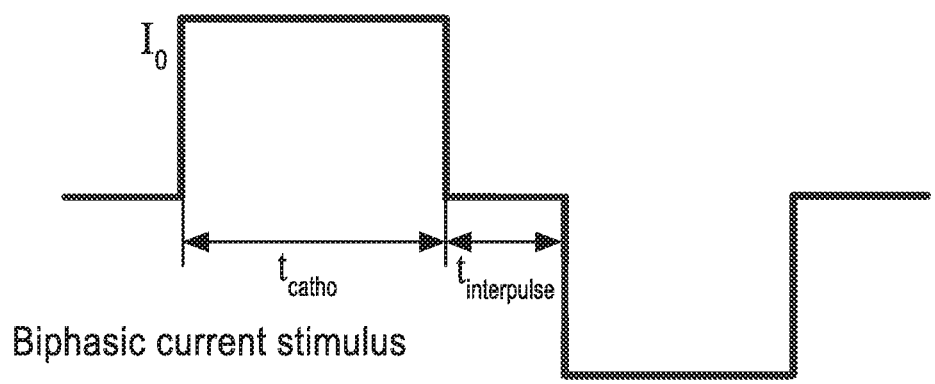

FIG. 10A and FIG. 10B illustrate utilizing a low-intensity, short-period bi-phasic current stimulus with a deliberately inserted interpulse delay in FIG. 10B, with its response seen in FIG. 10A. It is important to note that the pulse width and intensity of the stimulus in FIG. 10A is set to be small so that it does incur pure capacitive charge only which results in a linear increase in electrode overpotential while a conventional current stimulus with higher intensity or long pulse would result in both capacitive and faradic charge transfer as illustrated in FIG. 9B, complicating the process of acquiring the Randles cell electrode model. Using a small and short stimulus can minimize the fraction of Faradic current, allowing the estimation of $C_{dl}$ performed by simply measuring the resulting electrode voltage at the end of the leading pulse (shown as $V_1$ in FIG. 10A). Subsequently, during interpulse delay $t_{interpulse}$, the charge stored in $C_{dl}$ is passively discharged and the resulting electrode potential $V_e$ is given by:

$$V_e = (V_1 - I_0 R_S)\left(\frac{-t}{e^{R_{CT} \times C_{dl}}}\right). \tag{3}$$

$R_{CT}$ can thus be derived as:

$$R_{CT} = \frac{-t_{interpulse}}{\left(C_{dl} \ln\left(\frac{V_e}{V_1 - I_0 R_S}\right)\right)}. \tag{4}$$

Insertion of the interpulse delay provides a controlled discharge time and a known timing to sample the electrode potential. Once the electrode voltage is acquired at the end of the interpulse period (shown as $V_2$ in FIG. 10A), $R_{CT}$ can be determined. Finally, a compensating pulse, seen in the latter half of FIG. 10B is applied to maintain charge balance. Otherwise, accumulated residual charge might result in a DC offset at the electrode and the DC offset might affect the Faradic process, such as affecting $R_{CT}$, when frequent monitoring of the electrode impedance is performed.

The disclosed bio-impedance measurement technique is targeted at applications, including neural stimulators that deliver electric charge to activate neurons whose operation can be benefited in response to determining bio-impedance at the electrode-electrolyte/tissue interface.

Figure 11A:
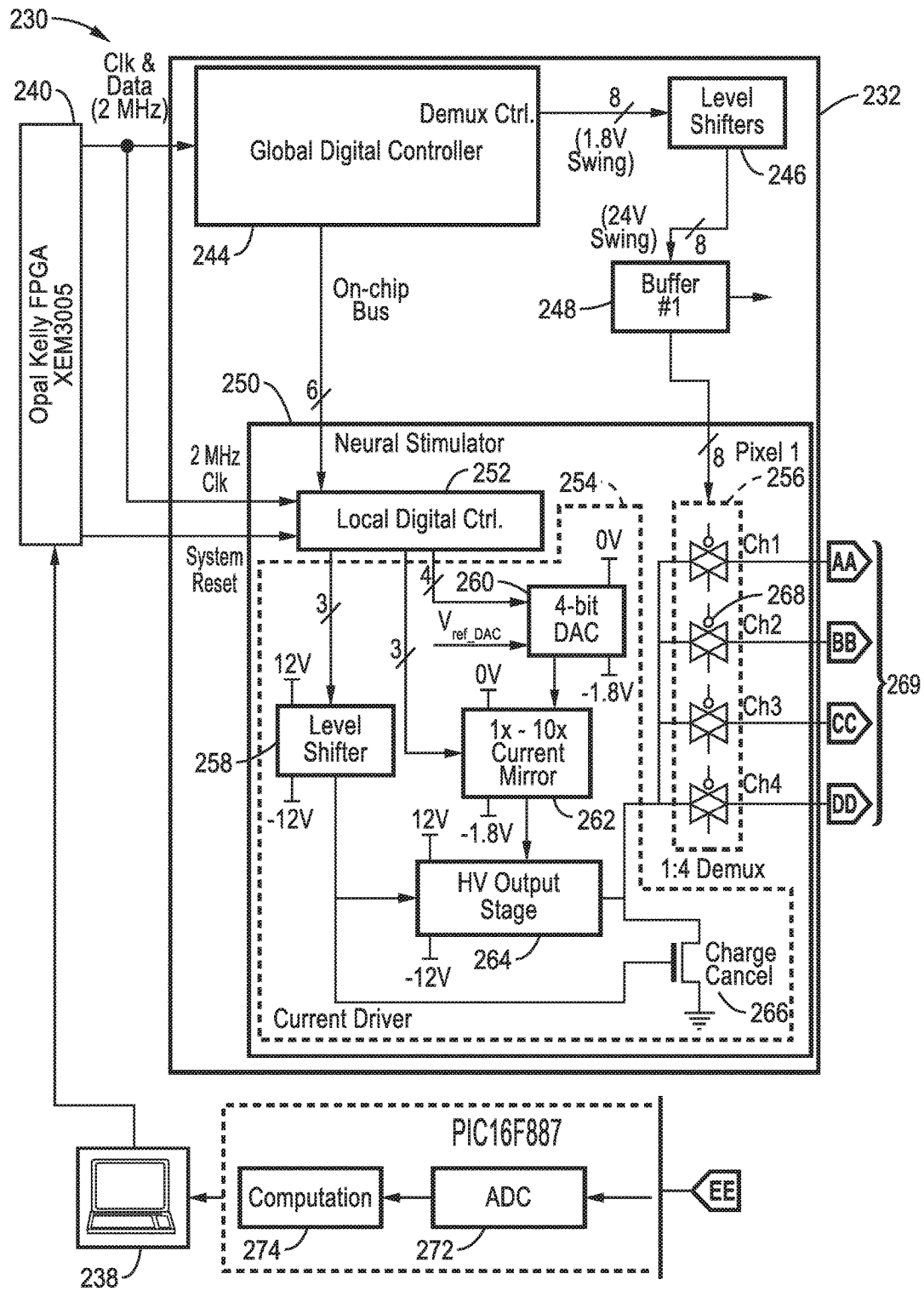
FIG. 11A and FIG. 11B are a schematic of a multi-channel neural stimulator utilizing a system-on-chip (SoC), which determines bio-impedance.
Figure 11B:
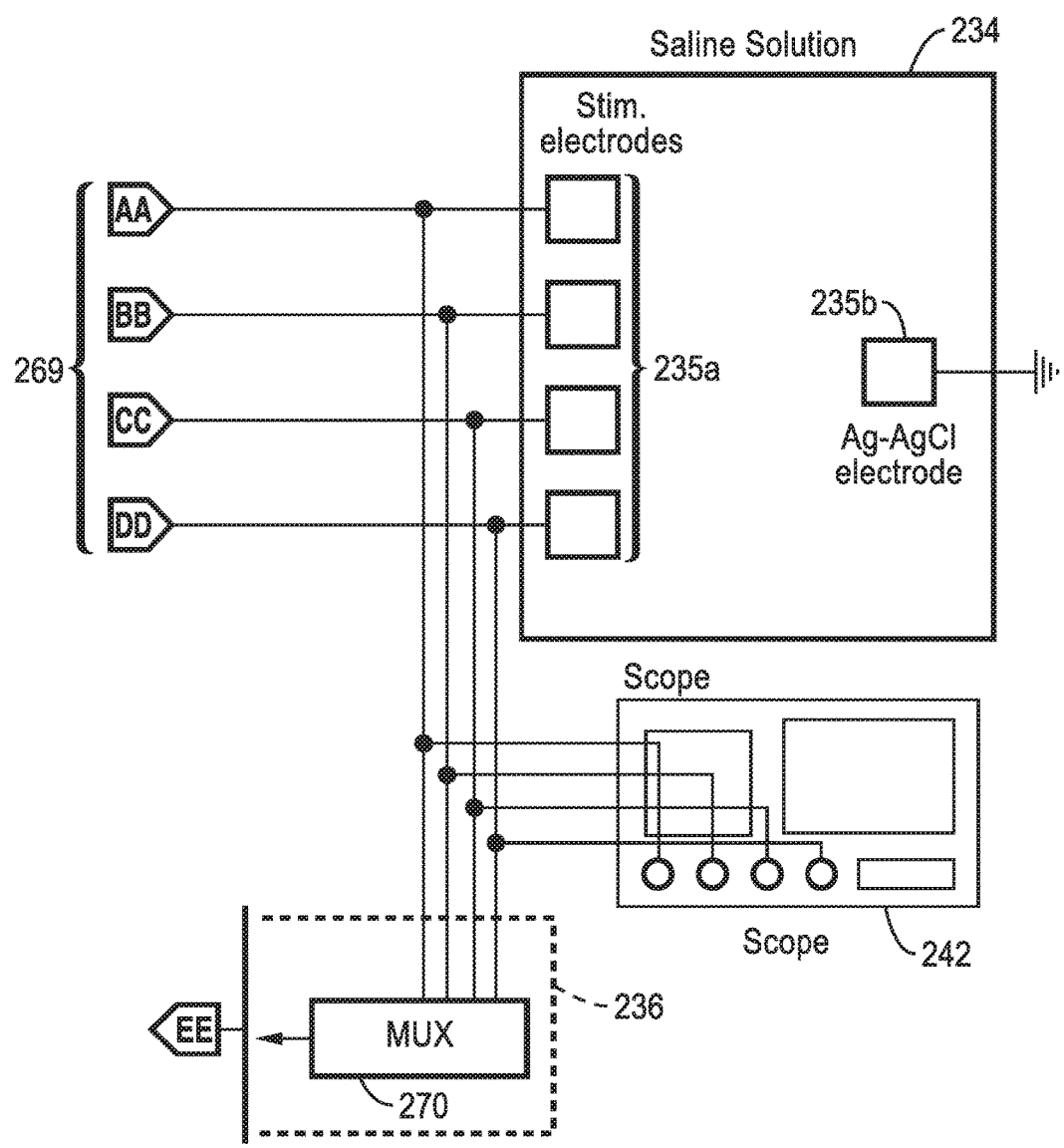

FIG. 11A and FIG. 11B are an example embodiment 230 of a multi-channel neural stimulator utilizing a system-on-chip (SoC) 232 which we developed to generate bi-phasic current stimulus with programmable pulse polarity, intensity, pulse width, and interpulse delay to a group of electrodes 234, such as comprising stimulus electrodes 235a, and a ground electrode 235b. By way of example and not limitation, the electrodes may comprise Ag—AgCl electrodes. Control electronics 236 are shown for registering information from SoC output, which by way of example is also seen coupled to a display device (i.e., oscilloscope).

A FPGA 240 was programmed to send stimulation command to SoC 232. One of ordinary skill in the art will recognize that the FPGA can be replaced by other circuitry, such as processors (MCU, DSP, ASIC, other forms of control circuitry and combinations thereof, without departing from the teachings of the invention. Digital control circuits of the SoC are shown by example with global digital controller 244, level shifters 246, and a first buffer 248 (within multiple buffers as desired) to decode commands and control neural stimulator 250, which is configured to generate a desired current stimulus. Neural stimulator 250 is shown with local digital control 252, a current driver 254, and a demultiplexer 256. The current driver 254 of the stimulator is depicted in this example as comprising a level shifter 258 for translating logic levels for controlling a high voltage (HV) output stage 264, and charge canceling circuit (e.g., transistor) 266. Bits from local control circuit also drive a digital-to-analog (DAC) converter 260 (e.g., 4-bit DAC) whose output drives a current mirror 262, whose output controls the HV output stage 264. Each output HV output stage is connected to 1to-4 demultiplexer 256, which expands the number of the output channel of the stimulator (i.e., 40 HV output stages build a 160 channel stimulator). Demultiplexer 256 is shown with high voltage drivers/buffers 268 directed to outputs 269, configured for coupling to the electrodes.

Outputs are captured and processed by circuit 236, depicted as comprising a multiplexer 270, analog-to-digital converter (ADC) 272, and a computation circuit 274 for processing the measured waveform information into a bio-impedance measurement. The processing of digital outputs from the ADC into bio-impedance measurements can be performed by different forms of digital circuitry, such as any desired combination of discrete logic, programmable arrays, application specific integrated circuits, or programming elements. In the example shown, a microcontroller (e.g., PIC16F887 from Microchip Tech. Inc.) is utilized for multiplexing 270 the acquired transient electrode voltage, converting the analog signal to digital 272 (e.g., built-in 10-bit ADC), and for processing the signals to determine bio-impedance. In the example shown, the ADC was set to sample only three voltages ($V_0$, $V_1$, and $V_2$). The sampling operation of the microcontroller in this example is triggered by a synchronization signal from the SoC, in which the synchronization signal was implemented using unused stimulation channel, although these elements can be synchronized using any desired synchronizing circuitry (e.g., clocks, timers, counters, digital logic, other electronic circuits and combinations thereof). Output from circuit 236 is shown for capture and/or display on an external display 238, and/or combination of computer processor and display. An oscilloscope 242 was also used to monitor the evoked potential during stimulation.

It should be appreciated that collecting and processing to arrive at bio-impedance measurements according to the presented technology can be readily implemented within various forms of digital circuitry. It should also be appreciated that such data processing is most readily implemented utilizing one or more computer processor devices (e.g., CPU, microprocessor, microcontroller, computer enabled ASIC, etc.) and associated memory (e.g., RAM, DRAM, NVRAM, FLASH, computer readable media, etc.) whereby instruction codes (programming) stored in the memory and executable on the processor perform the steps of the various process methods described herein. The presented technology is non-limiting with regard to memory and computer-readable media, insofar as these are non-transitory, and thus not constituting a transitory electronic signal.

In order to validate the disclosed impedance measurement method, two verification tests were conducted. In the first tests, the disclosed method was applied onto an emulated Randles cell made of discrete components with known values. In the second test, the impedance of a custom-made electrode developed at UCLA was evaluated. The stimulation electrodes and an Ag—AgCl reference electrode (e.g., P-BMP-1, ALA scientific instruments, NY) were dipped into a phosphate buffered saline (PBS) solution (concentration of 0.9% sodium chloride). Meanwhile, the impedance of the electrode was also measured using the same set-up through an impedance analyzer (HP 4194A) for verification and comparison.

The values of each discrete component of the emulated Randles cell ($R_{CT}$, $R_S$, $C_{dl}$) are 100 kΩ, 10 kΩ, and 30 nF, respectively. Bi-phasic stimuli was applied with an intensity of 10 µA and 100 µA, pulse width of 1 ms, and interpulse delay of 1 ms to this circuit model and the demanded resulting voltages were measured.

Figure 12A:
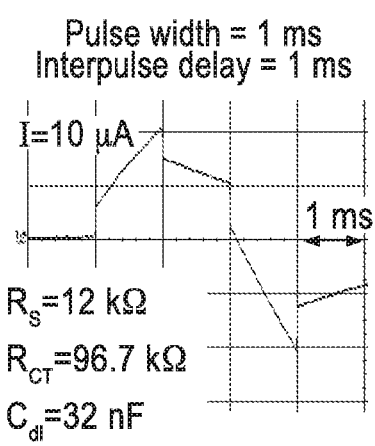
FIG. 12A and FIG. 12B are waveform diagrams of electrode response to bi-phasic current stimulus within interpulse delay at two different intensity levels.
Figure 12B:
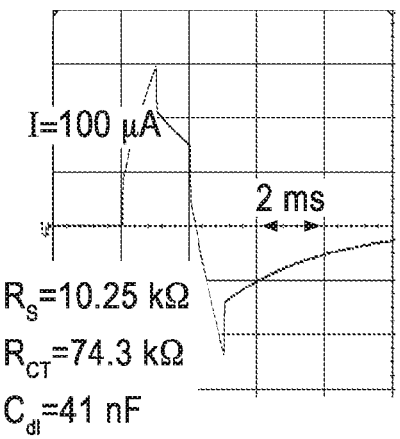

FIG. 12A and FIG. 12B depict measured waveforms of two respective resulting electrode voltages and the estimated component values are shown in these plots as $R_{CT}$=96.7 kΩ, $R_S$=12 kΩ, $C_{dl}$=32 nF at 10 µA, and $R_{CT}$=74.3 kΩ, $R_S$=10.25 kΩ, $C_{dl}$=41 nF at 100 µA). It can be seen that using small stimulus current provides a more accurate result, while a larger discrepancy from the nominal value of these $R_{CT}$ and $C_{dl}$ is exhibited when utilizing a large stimulus. There is also a slight inconsistency in the estimation of $R_S$. This is possibly due to the non-linearity of the stimulator driver.

In at least one of the embodiments, a 3×9 platinum polyimide electrode array was utilized for evaluating the disclosed technique. An electrode array was utilized in which each contact of the electrode shown has a diameter of 46.7 µm. Impedance was measured of a 3×9 platinum electrode array made on a flexible polyimide substrate. An Omnectics® connector was used to connect the electrode to the stimulator output. Each single electrode has an area of approximately 200 µm×500 µm with 40 exposed circular regions. $R_{CT}$, $R_S$, and $C_{dl}$ of the electrode were first characterized and extrapolated as approximately 1.8 kΩ, 15 kΩ, and 176 nF using HP 4194A. Subsequently, bi-phasic stimulus was injected into the electrode.

Figure 13A:
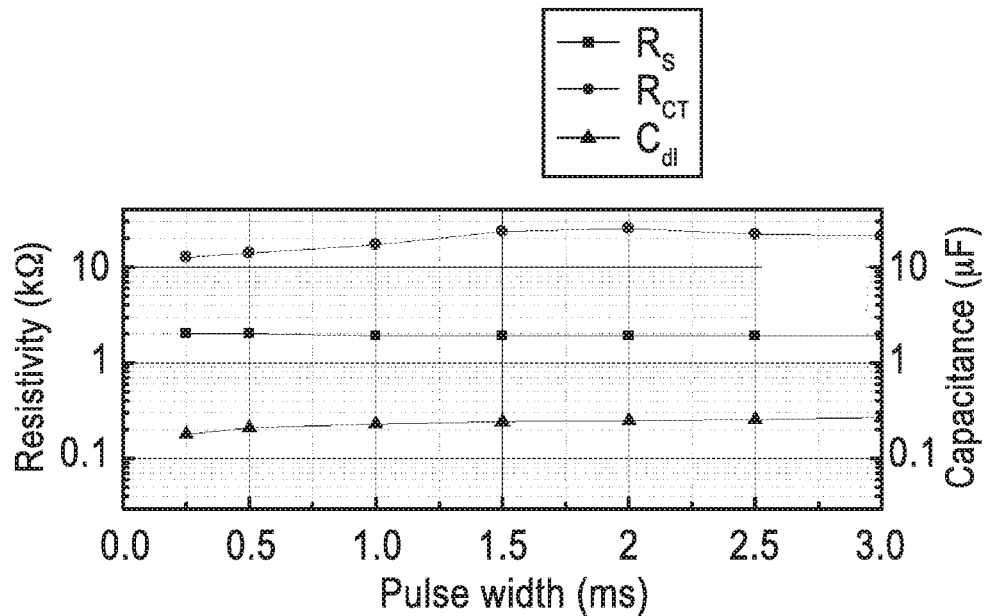
FIG. 13A and FIG. 13B are plots of estimated circuit parameters of an electrode comparing varied pulse width and intensity.
Figure 13B:
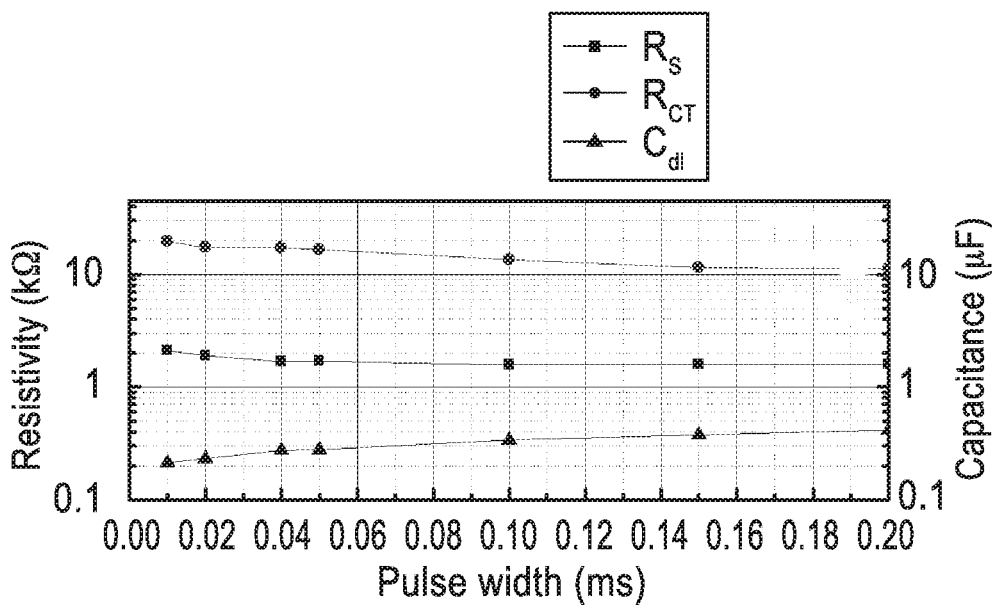

FIG. 13A and FIG. 13B depict estimated circuit parameters of the electrode based on varied stimulus pulse width and stimulus intensity, respectively. It can be seen that estimated $R_S$ is in the range of $R_S$ 1.9-2.0 kΩ, close to the results from HP4194A. However, as stimulus pulse width and intensity increases, more charge is delivered to the electrode to escalate the electrode overpotential. Therefore, Faradic current gradually increase and it affects the estimation of $C_{dl}$ and $R_{CT}$. The result and observation imply that using a small stimulus current is preferred in order to accurately estimate parameters of the equivalent circuits model of the electrode. It should also be noted that there is deviation in our measured $R_{CT}$ and $C_{dl}$, compared with results from HP 4191A. This is possibly due to the fact that large signal analysis is being performed, instead of small signal analysis.

Figure 14:
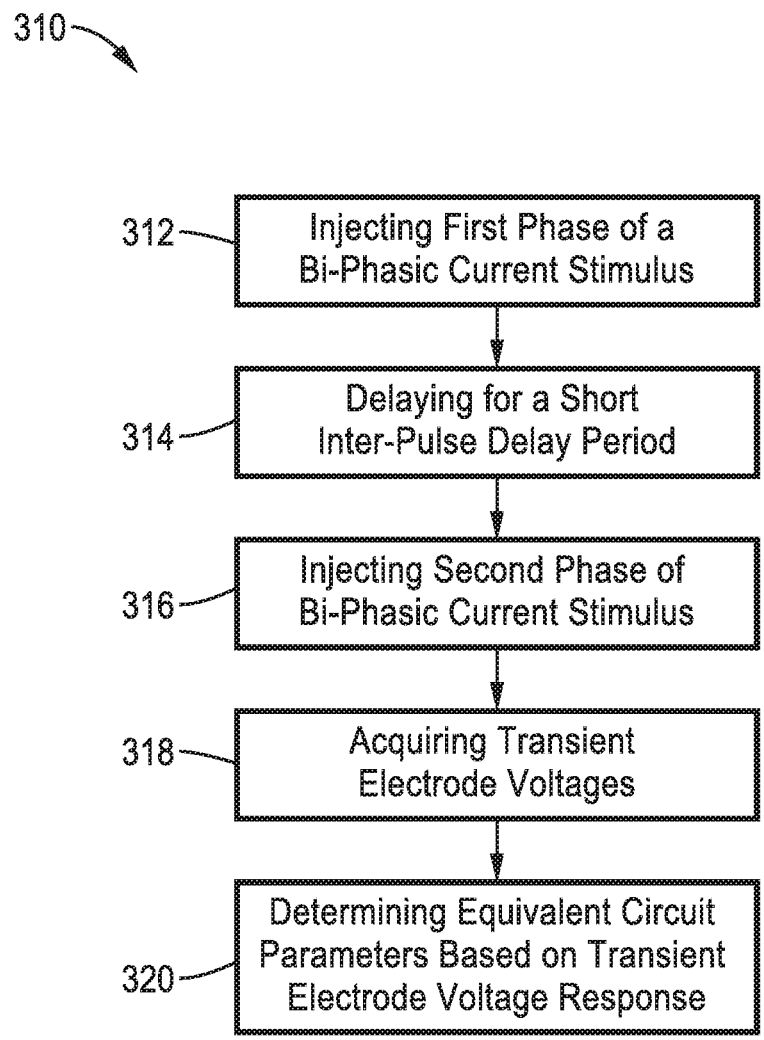
FIG. 14 is a flow diagram of a method for determining bio-impedance using a bi-phasic current stimulus.

FIG. 14 illustrates an example embodiment 310 of bio-impedance measurement of the present disclosure. A bi-phasic current stimulus is seen being injected having a first phase 312, an inter-pulse delay 314, and a second phase 316. Transient electrode voltages are registered 318, such as at least three selected points along the first phase and inter-pulse delay (e.g., beginning and end of first phase and end of inter-pulse delay). Once voltages are converted to digital signals they are processed 320 to determine equivalent circuit parameters.

The material of the tested electrode in at least one embodiment is platinum that is known to have a pseudo-capacity. However, for a capacitive electrode, such as titanium nitride and tantalum oxide, the proposed method can also be applied to estimate $C_{dl}$ and $R_S$. Moreover, unlike other impedance measurement approaches used in implantable neural stimulator, the proposed method can yield values for both $C_{dl}$ and $R_{CT}$, instead of $R_S$ only. With the knowledge of $C_{dl}$ and $R_{CT}$, an upper safe bound of the stimulus intensity and pulse width can be set to ensure the electrode overpotential does not exceed its water window.

Thus, it has been seen that bi-phasic current excitation is described for use in measuring and estimating equivalent circuits parameters of the Randles cell electrode model. A proof-of-concept system made of a stimulator SoC and a microcontroller/FPGA were implemented to generate the required stimulus and to perform electrode voltage acquisition. Leveraging on the dominating capacitive charging characteristic of the electrode when the electrode overpotential is small, double layer capacitance can be yielded by injecting a small current and measuring the electrode voltage. Through the known double layer capacitance and sampling of electrode voltage, the Faradic charge transfer resistance can be derived through the insertion of a predetermined discharge time. The electrode transient voltage needs to be sampled only three times and does not require sophisticated computation and hardware, making this approach attractive for implantable stimulators and commercial neural stimulators.

In addition, the measured electrode transient voltage or said bio-impedance can be used as a novel means to monitor/track the smooth muscle activity of gastrointestinal track or vascular blood vessel, providing viable physiological signals.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors. It will further be appreciated that as used herein, that the terms processor, central processing unit (CPU), and computer are used synonymously to denote a device capable of executing the programming and communication with input/output interfaces and/or peripheral devices.

From the description herein, it will be appreciated that that the present disclosure encompasses multiple embodiments which include, but are not limited to, the following:

1. An electrophysiological electrical stimulation and recording apparatus with stimulation artifact suppression, comprising: (a) a control circuit configured for controlling stimulus generation, artifact suppression and recording of a response to the generated stimulus; (b) a current mode neural stimulator coupled to said control circuit, for amplifying an output from the control circuit to a recording/STI electrode; (c) a first response amplification stage configured for amplifying the difference between a reference electrode and said recording/STI electrode as a measured stimulus response signal without amplifier saturation; (d) a second response amplification stage configured for amplifying the difference between said measured stimulus response signal and a subtraction signal selected by said control circuit; (e) wherein said control circuit is configured for: (e)(i) setting said subtraction signal to a fixed reference voltage; (e)(ii) generating a stimulus signal to said stimulus amplifier and storing an output from said second response amplification stage as a first artifact template; (e)(iii) calibrating the first artifact template by generating a stimulus signal to said stimulus amplifier while outputting said first artifact template as said subtraction signal to said second response amplification stage whose output is used to calibrate said first artifact template as a second artifact template; and (e)(iv) performing simultaneous stimulation and measurements by outputting said second artifact template as said subtraction signal to said second response amplification stage when outputting a stimulus signals to said stimulus amplifier connected to said recording/STI electrode; (e)(v) wherein subtraction of said second artifact template from the measured stimulus response signal results in removal of the artifacts from the measured stimulus response signal.

2. The apparatus of any preceding embodiment, wherein different electrodes are utilized for stimulation and recording.

3. The apparatus of any preceding embodiment, wherein the same electrode is utilized for both stimulation or recording.

4. The apparatus of any preceding embodiment, wherein calibrating the first artifact template can be performed any desired number of times to obtain a desired accuracy.

5. The apparatus of any preceding embodiment, wherein said first artifact template and said second artifact template are output as a waveform to said subtraction signal and timed in synchronization to said stimulus signal being generated to said stimulus amplifier.

6. The apparatus of any preceding embodiment, wherein a switching selector is controlled by said control circuit to select which signals are coupled to said second amplifier stage.

7. The apparatus of any preceding embodiment, wherein said apparatus separates artifact and neural signals even if they overlap in the time domain.

8. The apparatus of any preceding embodiment, wherein said apparatus provides stimulation artifact suppression even when a signal of interest and the stimulus are close together in a frequency domain.

9. The apparatus of any preceding embodiment, wherein said apparatus can generate an accurate artifact without a neural signal.

10. The apparatus of any preceding embodiment, wherein amplifier saturation is avoided thus allowing for additional post-signal processing.

11. The apparatus of any preceding embodiment, wherein said artifact template is refreshed periodically since the electrode-tissue interface is non-linear.

12. The apparatus of any preceding embodiment, wherein said control circuitry comprises a computer processor, memory, and digital-to-analog and analog-to-digital conversion circuitry.

13. The apparatus of any preceding embodiment, wherein said apparatus is integrated into an integrated circuit or system-on-chip (SoC).

14. A system for artifact removal/reduction, the system comprising: (a) a first amplifier having a first input configured to be connected to a working electrode, a second input configured to be connected to a reference electrode, and a second amplifier output; (b) a second amplifier having a first input configured to be connected to a reference voltage source, a second input connected to the output of the first amplifier through a switch, and a second amplifier output; (c) an analog-to-digital converter (ADC) having an input and an output; (d) a digital-to-analog converter (DAC) having an input and an output; (e) a stimulator having an input and an output; and (f) a microcontroller unit (MCU) having an input and an output; (g) wherein the output of the second amplifier is connected to the input of the analog to digital converter; (h) wherein the output of the first amplifier is connected to the microcontroller unit; (i) wherein the output of the analog to digital converter is configured to provide a digital signal to a signal processor; (j) wherein the input of the stimulator is connected to the microcontroller unit; (k) wherein the output of the stimulator is connected to the first input of the first amplifier through a switch; (l) wherein the input of the digital-to-analog converter is connected to the microcontroller unit; and (m) wherein the output of the digital-to-analog converter is connected to the first input of the second amplifier through a switch.

15. The system of any preceding embodiment, wherein the system has a first phase of operation comprising: (a) sending a command from the microcontroller unit to the stimulator to send a stimulus into a target area of tissue; (b) receiving artifact and neural responses to the stimulus; (c) wherein the first amplifier is configured as a unit gain buffer for artifact buffering; (d) wherein the microcontroller unit digitizes received artifact and neural responses; (e) wherein small neural signals can be filtered out by setting the least significant bit of the analog-to-digital converter to be larger than the amplitude of neural signals; (f) wherein a digitized artifact is stored in memory in the microcontroller unit.

16. The system of any preceding embodiment, wherein the system has a second phase of operation comprising: (a) activating the second amplifier configured as a unit-gain buffer; (b) sending a second stimulus; (c) converting the stored artifact to an analog waveform using the digital-to-analog converter and passing the analog waveform to the first input of the second amplifier as a reconstructed artifact; (d) wherein the artifact signal and reconstructed artifact are subsequently subtracted inside the second amplifier with its output digitized and stored in the microcontroller unit; (e) wherein the second amplifier produces an output that reflects the difference between the real artifact and the reconstructed artifact.

17. The system of any preceding embodiment, wherein the system has a third phase of operation comprising: (a) performing simultaneous recording and stimulation; (b) wherein the microcontroller unit outputs the calibrated artifact to cancel the real artifact; (c) wherein by applying the calibrated artifact to the second amplifier, the residual artifact is reduced; (d) wherein reduced artifact amplitude prevents amplifier saturation to preserve the neural signal during and after a electrical stimulus is applied.

18. The system of any preceding embodiment, or claim 16, or claim 17, further comprising programming executable by the microcontroller unit for performing one or more of said steps of operation in said first, second or third phases of operation.

19. The system of any preceding embodiment, wherein said system is integrated into an integrated circuit or system-on-chip (SoC).

20. A method of stimulation artifact suppression during electrophysiological electrical stimulation and recording, comprising: (a) controlling stimulus generation, artifact suppression and recording of a response to the generated stimulus within a control circuit; (b) amplifying in a stimulus amplifier an output from the control circuit to a recording/STI electrode during current mode neural stimulation; (c) amplifying the difference between a reference electrode and said recording/STI electrode as a measured stimulus response signal without amplifier saturation in a first response amplification stage; (d) amplifying the difference between said measured stimulus response signal and a subtraction signal selected by said control circuit in a second response amplification stage; (e) setting said subtraction signal to a fixed reference voltage; (f) generating a stimulus signal to said stimulus amplifier and storing an output from said second response amplification stage as a first artifact template; (g) calibrating the first artifact template by generating a stimulus signal to said stimulus amplifier while outputting said first artifact template as said subtraction signal to said second response amplification stage whose output is used to calibrate said first artifact template as a second artifact template; (h) performing simultaneous stimulation and measurements by outputting said second artifact template as said subtraction signal to said second response amplification stage when outputting a stimulus signals to said stimulus amplifier connected to said recording/STI electrode; and (i) wherein subtraction of said second artifact template from the measured stimulus response signal results in removal of the artifacts from the measured stimulus response signal.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An electrophysiological electrical stimulation and recording apparatus with stimulation artifact suppression, comprising:
   (a) a control circuit configured for controlling stimulus generation, artifact suppression and recording of a response to the generated stimulus;
   (b) a current mode neural stimulator coupled to said control circuit, for amplifying an output from the control circuit to a recording/STI electrode;
   (c) a first response amplification stage configured for amplifying the difference between a reference electrode and said recording/STI electrode as a measured stimulus response signal without amplifier saturation;
   (d) a second response amplification stage configured for amplifying the difference between said measured stimulus response signal and a subtraction signal selected by said control circuit;
   (e) wherein said control circuit is configured for:
      (i) setting said subtraction signal to a fixed reference voltage;
      (ii) generating a stimulus signal to said stimulus amplifier and storing an output from said second response amplification stage as a first artifact template;

(iii) calibrating the first artifact template by generating a stimulus signal to said stimulus amplifier while outputting said first artifact template as said subtraction signal to said second response amplification stage whose output is used to calibrate said first artifact template as a second artifact template; and (iv) performing simultaneous stimulation and measurements by outputting said second artifact template as said subtraction signal to said second response amplification stage when outputting a stimulus signals to said stimulus amplifier connected to said recording/STI electrode;

(v) wherein subtraction of said second artifact template from the measured stimulus response signal results in removal of the artifacts from the measured stimulus response signal.

2. The apparatus as recited in claim 1, wherein different electrodes are utilized for stimulation and recording.

3. The apparatus as recited in claim 1, wherein the same electrode is utilized for both stimulation or recording.

4. The apparatus as recited in claim 1, wherein calibrating the first artifact template can be performed any desired number of times to obtain a desired accuracy.

5. The apparatus as recited in claim 1, wherein said first artifact template and said second artifact template are output as a waveform to said subtraction signal and timed in synchronization to said stimulus signal being generated to said stimulus amplifier.

6. The apparatus as recited in claim 1, wherein a switching selector is controlled by said control circuit to select which signals are coupled to said second amplifier stage.

7. The apparatus as recited in claim 1, wherein said apparatus separates artifact and neural signals even if they overlap in the time domain.

8. The apparatus as recited in claim 1, wherein said apparatus provides stimulation artifact suppression even when a signal of interest and the stimulus are close together in a frequency domain.

9. The apparatus as recited in claim 1, wherein said apparatus can generate an accurate artifact without a neural signal.

10. The apparatus as recited in claim 1, wherein amplifier saturation is avoided thus allowing for additional post-signal processing.

11. The apparatus as recited in claim 1, wherein said artifact template is refreshed periodically since the electrode-tissue interface is non-linear.

12. The apparatus as recited in claim 1, wherein said control circuitry comprises a computer processor, memory, and digital-to-analog and analog-to-digital conversion circuitry.

13. The apparatus as recited in claim 1, wherein said apparatus is integrated into an integrated circuit or system-on-chip (SoC).

14. A method of stimulation artifact suppression during electrophysiological electrical stimulation and recording, comprising:

(a) controlling stimulus generation, artifact suppression and recording of a response to the generated stimulus within a control circuit;

(b) amplifying in a stimulus amplifier an output from the control circuit to a recording/STI electrode during current mode neural stimulation;

(c) amplifying the difference between a reference electrode and said recording/STI electrode as a measured stimulus response signal without amplifier saturation in a first response amplification stage;

(d) amplifying the difference between said measured stimulus response signal and a subtraction signal selected by said control circuit in a second response amplification stage;

(e) setting said subtraction signal to a fixed reference voltage;

(f) generating a stimulus signal to said stimulus amplifier and storing an output from said second response amplification stage as a first artifact template;

(g) calibrating the first artifact template by generating a stimulus signal to said stimulus amplifier while outputting said first artifact template as said subtraction signal to said second response amplification stage whose output is used to calibrate said first artifact template as a second artifact template;

(h) performing simultaneous stimulation and measurements by outputting said second artifact template as said subtraction signal to said second response amplification stage when outputting a stimulus signals to said stimulus amplifier connected to said recording/STI electrode; and (i) wherein subtraction of said second artifact template from the measured stimulus response signal results in removal of the artifacts from the measured stimulus response signal.

* * * * *